(12) United States Patent
Hughes-Fulford

(10) Patent No.: US 11,266,676 B2
(45) Date of Patent: Mar. 8, 2022

(54) MICRORNA IN T CELL ACTIVATION

(71) Applicants: THE UNITED STATES OF AMERICA as represented by THE DEPARTMENT OF VETERANS AFFAIRS, Washington, DC (US); THE REGENTS OF THE UNIVERSITY OF CALIFORNIA, Oakland, CA (US)

(72) Inventor: Millie Hughes-Fulford, San Francisco, CA (US)

(73) Assignees: The Regents of the University of California; The United States Government as represented by the Department of Veterans Affairs

( * ) Notice: Subject to any disclaimer, the term of this patent is extended or adjusted under 35 U.S.C. 154(b) by 0 days.

(21) Appl. No.: 16/345,512

(22) PCT Filed: Oct. 27, 2017

(86) PCT No.: PCT/US2017/058852
§ 371 (c)(1),
(2) Date: Apr. 26, 2019

(87) PCT Pub. No.: WO2018/081624
PCT Pub. Date: May 3, 2018

(65) Prior Publication Data
US 2019/0307786 A1    Oct. 10, 2019

Related U.S. Application Data

(60) Provisional application No. 62/413,714, filed on Oct. 27, 2016.

(51) Int. Cl.
| | | |
|---|---|---|
| C07H 21/02 | (2006.01) |
| C07H 21/04 | (2006.01) |
| A61K 31/7105 | (2006.01) |
| A61P 37/06 | (2006.01) |
| C12Q 1/6874 | (2018.01) |
| C12Q 1/6883 | (2018.01) |
| C12N 15/113 | (2010.01) |

(52) U.S. Cl.
CPC .......... *A61K 31/7105* (2013.01); *A61P 37/06* (2018.01); *C12N 15/113* (2013.01); *C12Q 1/6874* (2013.01); *C12Q 1/6883* (2013.01); *C12N 2310/141* (2013.01); *C12N 2330/10* (2013.01); *C12Q 2600/178* (2013.01)

(58) Field of Classification Search
CPC ........ C12Q 2600/178; C12N 2310/141; C12N 15/113
See application file for complete search history.

(56) References Cited

PUBLICATIONS

Gandhi (Multiple Sclerosis Journal, 2015, 21(9), 1095-1103).*

* cited by examiner

*Primary Examiner* — Amy H Bowman
(74) *Attorney, Agent, or Firm* — Ballard Spahr LLP

(57) ABSTRACT

Disclosed herein are methods for treating an immune system condition and/or altering T cell activation in a subject. Also disclosed herein are methods for diagnosing an immune system condition in a subject. In some examples, the methods can include measuring expression of at least one T cell activation-related miRNA in a sample obtained from a subject. The methods further include administering to the subject a therapeutically effective amount of an miRNA or mimic thereof, and/or an inhibitor of miRNA or mimic thereof and/or administering to the subject T cells contacted with an effective amount of miRNA or mimic thereof, and/or an inhibitor of miRNA or mimic thereof.

9 Claims, 5 Drawing Sheets
Specification includes a Sequence Listing.

FIG. 3

| Gene | NT | | CA 1g | | CA ug | | Fold Increase 1g/NT | Fold Increase ug/NT | Fold Increase 1g/ug | Percent of 1g |
|---|---|---|---|---|---|---|---|---|---|---|
| | Average | SD | Average | SD | Average | SD | | | | |
| IL-2 | 2.16 | 1.03 | 3493.94 | 908.88 | 1544.67 | 638.29 | 1620.92 *** | 716.61 * | 2.26 ** | 44.21 |
| NFKBIA | 306.74 | 157.60 | 2315.19 | 1057.12 | 1236.70 | 387.22 | 7.55 ** | 4.03 | 1.87 * | 53.42 |
| CD69 | 12.79 | 11.81 | 1852.26 | 904.25 | 416.21 | 277.32 | 144.85 ** | 32.55 | 4.45 * | 22.47 |
| CD40LG | 37.58 | 17.61 | 1786.44 | 504.66 | 227.62 | 36.66 | 47.53 *** | 6.06 | 7.85 *** | 12.74 |
| IFNG | 0.25 | 0.31 | 1053.14 | 368.72 | 397.69 | 190.78 | 4188.59 *** | 1581.71 | 2.65 ** | 37.76 |
| TNFA | 10.09 | 1.75 | 1034.99 | 213.27 | 424.51 | 156.85 | 102.53 *** | 42.05 * | 2.44 ** | 41.02 |
| GMCSF | 0.46 | 0.25 | 919.69 | 467.75 | 308.44 | 98.38 | 1998.96 ** | 670.40 | 2.98 * | 33.54 |
| IRF4 | 6.27 | 0.34 | 280.86 | 82.44 | 105.83 | 6.92 | 44.83 *** | 16.89 | 2.65 ** | 37.68 |
| REL | 17.38 | 4.77 | 209.86 | 61.35 | 74.54 | 9.40 | 12.08 *** | 4.29 | 2.82 ** | 35.52 |
| BTG2 | 58.16 | 12.60 | 174.10 | 63.93 | 124.89 | 12.98 | 2.99 * | 2.15 | 1.39 | 71.74 |
| NR4A3 | 2.31 | 1.97 | 134.76 | 103.14 | 27.06 | 12.08 | 58.29 * | 11.71 | 4.98 | 20.08 |
| EGR1 | 5.92 | 3.74 | 126.02 | 42.00 | 57.99 | 9.36 | 21.28 ** | 9.79 | 2.17 * | 46.01 |
| TAGAP | 35.33 | 5.74 | 111.81 | 10.07 | 86.02 | 18.64 | 3.16 *** | 2.43 ** | 1.30 | 76.93 |
| IL2Ra | 13.48 | 4.58 | 101.68 | 22.31 | 26.13 | 7.36 | 7.54 *** | 1.94 | 3.89 *** | 25.70 |
| CREB1 | 49.58 | 10.42 | 47.92 | 7.80 | 52.16 | 16.18 | 0.97 | 1.05 | 0.92 | 108.86 |
| SRF | 9.07 | 1.65 | 21.38 | 2.85 | 25.46 | 7.23 | 2.36 * | 2.81 ** | 0.84 | 119.07 |
| SPRY2 | 2.46 | 0.45 | 2.55 | 1.39 | 4.82 | 1.79 | 1.03 | 1.96 | 0.53 | 189.48 |

MICRORNA IN T CELL ACTIVATION

CROSS REFERENCE TO RELATED APPLICATION

This application is a U.S. National Phase Application of International Application No. PCT/US2017/058852, filed on Oct. 27, 2017, which claims the benefit of U.S. Provisional Application No. 62/413,714, filed on Oct. 27, 2016, the contents of which are herein incorporated by reference in their entireties.

ACKNOWLEDGMENT OF GOVERNMENT SUPPORT

This invention was made with government support under grant number 5UH3AG037628 awarded by the National Institutes of Health and supplemented by the Center for the Advancement of Science in Space. The government has certain rights in the invention.

FIELD

The disclosure relates to immunology, particularly methods for treating subjects with immune system conditions.

BACKGROUND

Discovered in nematodes in 1993, microRNAs (miRNAs) are non-coding RNAs that are related to small interfering RNAs (siRNAs), the small RNAs that guide RNA interference (RNAi). miRNAs sculpt gene expression profiles during plant and animal development and may regulate as many as one-third of human genes. miRNAs are found only in plants and animals, and in the viruses that infect them. Each miRNA may have hundreds of targets, such as due to imperfect base pairing.

miRNAs function very much like siRNAs, but these two types of small RNAs can be distinguished by their distinct pathways for maturation (Du and Zamore, *Development (Cambridge)* 132:4645-4652, 2005). miRNA is made from larger pri-miRNA which is much longer than the processed mature miRNA molecule. Pri-miRNA has a cap and poly-A tail and is processed to short 70-nucleotide stem-loop structures in the cell nucleus. The pri-miRNA is processed by Drosha and made into pre-miRNA. The pre-miRNA is then exported to the cytoplasm by exportin-5 and processed further by the enzyme Dicer into mature miRNA. miRNA in the cytoplasm then combines to form a complex miRISA, which is guided to its mRNA target by the miRNA strand to match RNA targets.

Most miRNAs are 20-25 nucleotides long and are non-protein coding. The majority regulate gene expression by binding to the 3' untranslated region (UTR) of target mRNAs inducing translational repression of RNA and protein through mechanisms that are not fully understood. It has also been discovered that at least some miRNAs may increase gene expression through a process called RNA activation. In these cases, the miRNA appears to target a sequence in the gene promoter (e.g., Li et al., *Proc. Natl. Acad. Sci. USA* 103:17337-17342, 2006; Janowski et al., *Nature Chem. Biol.* 3:166-173, 2007; Schwartz et al., *Nature Struct. Mol. Biol.* 15:842-848, 2008).

Over 50% of the Apollo astronauts had bacterial or viral infections during flight, or within 1 week of landing. Apollo 7 marked humanity's first experience with spaceflight infection when all three crewmembers contracted head colds during their mission and on Apollo 13, one astronaut contracted *Pseudomonas aeruginosa* and suffered from intense chills and fever (Hawkins and Zeiglchmid, In *Biomedical Results of Apollo* (Johnston et al., eds.), pp. 43-81, NASA). *P. aeruginosa* is an opportunistic pathogen and rarely causes disease unless the person suffers from a break in epithelia or from immune suppression. As a result, the U.S. and Russian programs implemented pre-flight quarantine programs. Even with the precautions, one of the astronauts working on the International Space Station (ISS) had full body shingles while in orbit. Experiments from Skylab and Shuttle have confirmed that T-cells have a suppressed immune response (in vivo and in vitro) with lower T cell proliferation/activation, lower IL-2 synthesis, and severely reduced IL-2Ra expression (RNA and protein); these blunted immune responses are also seen in the immunosuppressed elderly (*Merck Manual of Geriatrics*, $3^{rd}$ edition and online addition, 2005). miRNAs may be up- or down-regulated in spaceflight (microgravity conditions) or during the aging process and may present targets for modulating immune responses.

SUMMARY

Disclosed herein are methods for treating an immune system condition in a subject. The methods can include measuring expression of at least one T cell activation-related miRNA in a sample obtained from a subject. In some examples, the at least one T cell activation-related miRNA includes at least one of mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p. The methods include measuring differential expression of the at least one T cell activation-related miRNA compared to a control representing expression of the at least one T cell activation-related miRNA in a subject or a population who does not have an immune system condition. The methods include administering at least one of miRNA therapy, other immunomodulatory therapy, non-steroidal anti-inflammatory drugs (NSAIDs), acetaminophen, corticosteroids, anti-inflammatory supplements, biologics, disease-modifying antirheumatic drugs (DMARDs), antimalarial drugs, stem cell or blood transfusion, physical therapy, and/or surgery, for example to a subject with differential expression of at least one T cell-activation related miRNA compared to the control, thereby treating the subject.

Also disclosed herein are methods for diagnosing an immune system condition in a subject. In some examples, the methods include measuring expression of at least one T cell activation-related miRNA in a sample obtained from a subject. In some examples, the at least one T cell activation-related miRNA includes at least one of mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p. The methods also include comparing the expression of the at least one T cell activation-related miRNA with a control representing expression of the at least one T cell activation-related miRNA in a subject or a population who does not have an immune system condition and determining that the subject has an immune system condition when differential expression of the T cell activation-related miRNA compared to the control is detected.

Further disclosed herein are methods for treating an immune system condition in a subject. In some examples, the methods include selecting a subject with an immune system condition. In specific examples, the immune system condition can be an underactive or an overactive immune response. The methods include administering to the subject a therapeutically effective amount of an miRNA or mimic thereof and/or an inhibitor of miRNA or mimic thereof, thereby treating the immune system condition. In specific, non-limiting examples, where the immune system condition includes an underactive immune response, the miRNA can include at least one of mir-326, mir-6860, miR-6860, mir-1976, mir-550b-1, mir-550b-2, miR-8071, miR-4481, and/or mir-3689b, or a mimic thereof and/or the inhibitor of miRNA can include an inhibitor of at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p or a mimic thereof. In other examples, where the immune system condition includes an overactive immune response, the an inhibitor of miRNA can include an inhibitor of at least one of mir-326, mir-6860, miR-6860, mir-1976, mir-550b-1, mir-550b-2, miR-8071, miR-4481, and/or mir-3689b or a mimic thereof and/or the miRNA includes at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p or a mimic thereof.

In additional embodiments of methods for treating an immune system condition in a subject, and where the immune system condition includes an underactive immune response, the methods include activating T cells and contacting the activated T cells with an effective amount of miRNA, including at least one of mir-326, mir-6860, miR-6860, mir-1976, mir-550b-1, mir-550b-2, miR-8071, miR-4481, and/or mir-3689b, or a mimic thereof and/or an inhibitor of miRNA, including an inhibitor of at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby treating the immune system condition. In other embodiments of methods for treating an immune system condition in a subject, and where the immune system condition includes an overactive immune response, the methods include contacting activated T cells with an effective amount of an inhibitor of miRNA, including an inhibitor of at least one of mir-326, mir-6860, miR-6860, mir-1976, mir-550b-1, mir-550b-2, miR-8071, miR-4481, and/or mir-3689b, or a mimic thereof, and/or miRNA, including at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby treating the immune system condition.

Also disclosed herein are methods for altering T cell activation (for example, increasing or decreasing T cell activation) in a subject. In some examples, the methods include selecting a subject with activated T cells. In specific, non-limiting examples, the methods include administering to the subject a therapeutically effective amount of miRNA, including at least one of mir-326, mir-6860, miR-6860, mir-1976, mir-550b-1, mir-550b-2, miR-8071, miR-4481, and/or mir-3689b, or a mimic thereof, and/or an inhibitor of miRNA, including an inhibitor of at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby increasing T cell activation as compared to a control. In other non-limiting examples, the methods include administering to the subject a therapeutically effective amount of an inhibitor of miRNA, including an inhibitor of at least one of mir-326, mir-6860, miR-6860, mir-1976, mir-550b-1, mir-550b-2, miR-8071, miR-4481, and/or mir-3689b, or a mimic thereof and/or miRNA, including at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby decreasing T cell activation as compared to a control.

Further disclosed herein are methods for altering T cell activation (for example, increasing or decreasing T cell activation) in a subject. In some examples, the methods can include activating T cells and contacting the activated T cells with an effective amount miRNA, including at least one of mir-326, mir-6860, miR-6860, mir-1976, mir-550b-1, mir-550b-2, miR-8071, miR-4481, and/or mir-3689b, or a mimic thereof, and/or an inhibitor of miRNA, including an inhibitor of at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby increasing T cell activation as compared to a control. In other examples, the methods include contacting activated T cells with an effective amount of an inhibitor of miRNA, including an inhibitor of at least one of mir-326, mir-6860, miR-6860, mir-1976, mir-550b-1, mir-550b-2, miR-8071, miR-4481, and/or mir-3689b, or a mimic thereof, and/or miRNA, including at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby decreasing the T cell activation as compared to a control.

The foregoing and other features of the disclosure will become more apparent from the following detailed description, which proceeds with reference to the accompanying figures.

BRIEF DESCRIPTION OF THE DRAWINGS

FIG. 3 is a table showing genes that are induced during T-cell activation at 1×g, some of which are targets of five of the miRNAs that are downregulated during T-cell activation at 1×g but that are not regulated during T-cell activation in microgravity (m); NT, untreated; CA, activated cells.

SEQUENCE LISTING

Figure 1A:
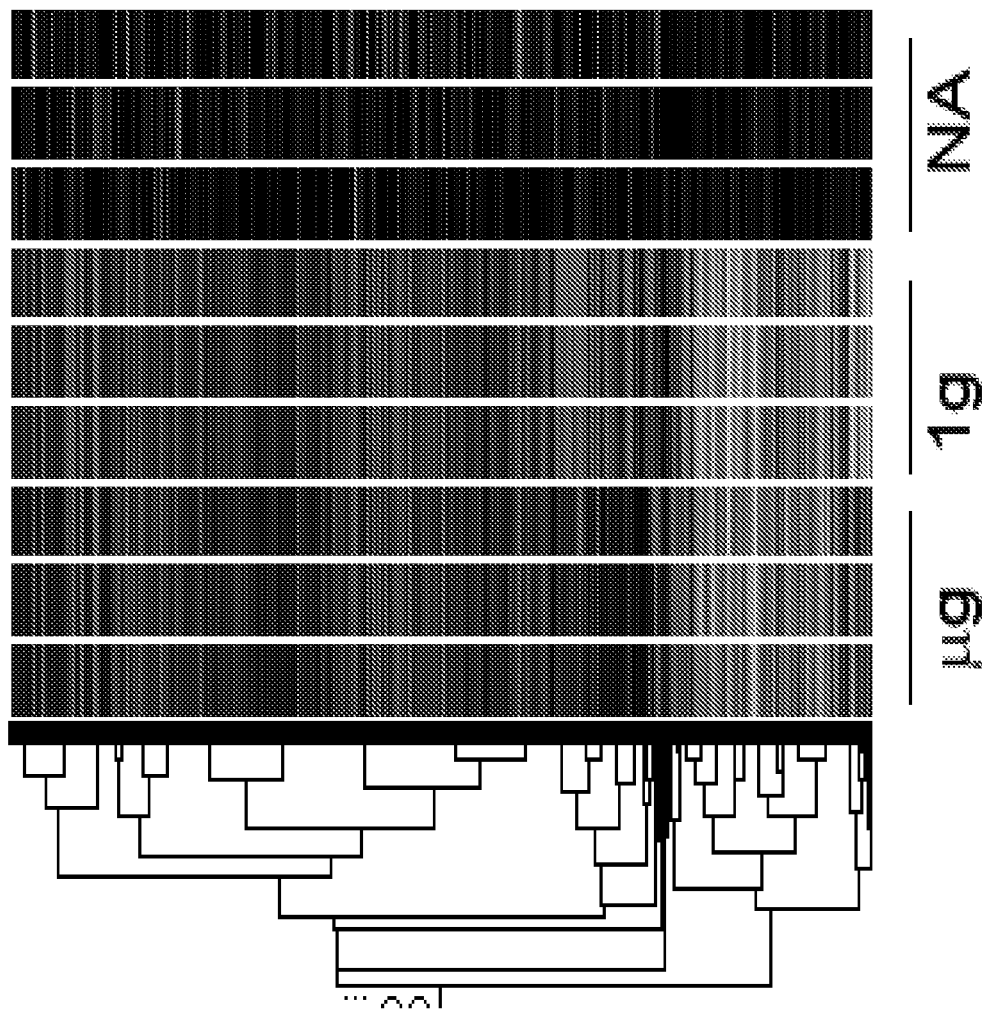
FIG. 1A is an mRNA expression Heat Map from Activation of T cells in spaceflight.

Any nucleic acid and amino acid sequences listed herein or in the accompanying sequence listing are shown using standard letter abbreviations for nucleotide bases and amino acids, as defined in 37 C.F.R. § 1.822. In at least some cases, only one strand of each nucleic acid sequence is shown, but the complementary strand is understood as included by any reference to the displayed strand.

SEQ ID NOs: 1-27 are exemplary miRNA nucleic acid sequences.

SEQ ID NO: 1 is an miRNA nucleic acid sequence of human miR-25-3p.

SEQ ID NO: 2 is an miRNA nucleic acid sequence of human mir-326.

SEQ ID NO: 3 is an miRNA nucleic acid sequence of mouse mir-326.

SEQ ID NO: 4 is an miRNA nucleic acid sequence of human miR-6860.

SEQ ID NO: 5 is an miRNA nucleic acid sequence of human miR-6860.

SEQ ID NO: 6 is an miRNA nucleic acid sequence of human mir-1976.

SEQ ID NO: 7 is an miRNA nucleic acid sequence of human mir-1976.

SEQ ID NO: 8 is an miRNA nucleic acid sequence of human mir-550b-1.

SEQ ID NO: 9 is an miRNA nucleic acid sequence of human mir-550b-2.

SEQ ID NO: 10 is an miRNA nucleic acid sequence of human miR-8071.

SEQ ID NO: 11 is an miRNA nucleic acid sequence of human miR-8071.

SEQ ID NO: 12 is an miRNA nucleic acid sequence of human miR-4481.

SEQ ID NO: 13 is an miRNA nucleic acid sequence of human miR-4481.

SEQ ID NO: 14 is an miRNA nucleic acid sequence of human miR-3689b.

SEQ ID NO: 15 is an miRNA nucleic acid sequence of human miR-3689b.

SEQ ID NO: 16 is an miRNA nucleic acid sequence of human miR-3689b.

SEQ ID NO: 17 is an miRNA nucleic acid sequence of human miR-629-3p.

SEQ ID NO: 18 is an miRNA nucleic acid sequence of human miR-330-3p.

SEQ ID NO: 19 is an miRNA nucleic acid sequence of mouse miR-330-3p.

SEQ ID NO: 20 is an miRNA nucleic acid sequence of human miR-501-3p.

SEQ ID NO: 21 is an miRNA nucleic acid sequence of mouse miR-501-3p.

SEQ ID NO: 22 is an miRNA nucleic acid sequence of human miR-7-1-3p.

SEQ ID NO: 23 is an miRNA nucleic acid sequence of human miR-128-3p.

SEQ ID NO: 24 is an miRNA nucleic acid sequence of human miR-26b-5p.

SEQ ID NO: 25 is an miRNA nucleic acid sequence of human miR-125b-5p.

SEQ ID NO: 26 is an miRNA nucleic acid sequence of human miR-99a-5p.

SEQ ID NO: 27 is an miRNA nucleic acid sequence of human miR-363-3p.

DETAILED DESCRIPTION

During spaceflight experiments, the inventor observed upregulation or downregulation of certain miRNAs during T cell activation in on-board gravity samples that were significantly activated in the gravity field. However, in microgravity, the T cell activation was blunted and these miRNAs were not significantly changed from the non-activated controls. These miRNAs (and miRNA mimics or anti-mimics) may be used to stimulate the immune system (for example, in older adults or individuals with a compromised immune system). Immunosuppression was also found in mice during spaceflight, suggesting a physiological dependence on gravity for adaptive immune response. This suggests that this characteristic is a common thread throughout the animal kingdom, since human and mouse immune systems appear to be at least partly dependent on gravity for full function.

As disclosed herein, the inventor has also discovered miRNAs that can ameliorate excessive immune response seen in autoimmune disease. Thus, the identified miRNAs may also be used to treat or inhibit autoimmune diseases, including rheumatoid arthritis, multiple sclerosis, chemokine/cytokine flares (such as cytokine storms), and Crohn's disease.

Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a protein" includes single or plural cells and is considered equivalent to the phrase "comprising at least one protein." The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references and GENBANK® Accession numbers cited herein are incorporated by reference.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

In order to facilitate review of the various embodiments of the disclosure, the following explanations of specific terms are provided.

Administration: To provide or give to a subject, such as a therapeutic drug, procedure, or protocol (e.g., for a subject with an immune system disorder). Exemplary routes of administration include, but are not limited to, oral, injection (such as subcutaneous, intramuscular, intradermal, intraperitoneal, intratumoral, intraprostatic, and intravenous), sublingual, rectal, transdermal, intranasal, and inhalation routes.

Autoimmune disorder: A disorder in which the immune system produces an immune response (e.g., a B cell or a T cell response) against an endogenous antigen, with consequent injury to tissues. The injury may be localized to certain organs, such as thyroiditis, or may involve a particular tissue at different locations, such as Goodpasture's disease, or may be systemic, such as lupus erythematosus.

In some examples, autoimmune diseases include systemic lupus erythematosus, Sjogren's syndrome, rheumatoid arthritis, type I diabetes mellitus, Wegener's granulomatosis, inflammatory bowel disease, polymyositis, dermatomyositis, multiple endocrine failure, Schmidt's syndrome, autoimmune uveitis, Addison's disease, adrenalitis, Graves' disease, thyroiditis, Hashimoto's thyroiditis, autoimmune thyroid disease, pernicious anemia, gastric atrophy, chronic hepatitis, lupoid hepatitis, atherosclerosis, presenile dementia, demyelinating diseases, multiple sclerosis, subacute cutaneous lupus erythematosus, hypoparathyroidism, Dressler's syndrome, myasthenia gravis, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), adult onset diabetes mellitus (Type II diabetes), male and female autoimmune infertility, ankylosing spondylitis, ulcerative colitis, Crohn's disease, mixed connective tissue disease, polyarteritis nedosa, systemic necrotizing vasculitis, juvenile onset rheumatoid arthritis, glomerulonephritis, atopic dermatitis, atopic rhinitis, Goodpasture's syndrome, Chagas' disease, sarcoidosis, rheumatic fever, asthma, recurrent abortion, anti-phospholipid syndrome, farmer's lung, erythema multiforme, post cardiotomy syndrome, Cushing's syndrome, autoimmune chronic active hepatitis, bird-fancier's lung, allergic disease, allergic encephalomyelitis, toxic epidermal necrolysis, alopecia, Alport's syndrome, alveolitis, allergic alveolitis, fibrosing alveolitis, interstitial lung disease, erythema nodosum, pyoderma gangrenosum, transfusion reaction, leprosy, malaria, leishmaniasis, trypanosomiasis, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, glomerulonephritis, graft versus host disease, transplantation rejection, human immunodeficiency virus infection, echovirus infection, cardiomyopathy, Alzheimer's disease, parvovirus infection, rubella virus infection, post vaccination syndromes, congenital rubella infection, Hodgkin's and Non-Hodgkin's lymphoma, renal cell carcinoma, multiple myeloma, Eaton-Lambert syndrome, relapsing polychondritis, malignant melanoma, cryoglobulinemia, Waldenstrom's macroglobulemia, Epstein-Barr virus infection, rubulavirus, and Evan's syndrome.

Chemokine (chemoattractant cytokine): A type of cytokine (a soluble molecule that a cell produces to control reactions between other cells) that specifically alters the behavior of leukocytes (white blood cells). Chemokines include CC chemokines, CXC chemokines, C chemokines, and $CX_3C$ chemokines. Examples include, but are not limited to, CCL3 and XCL2, and the like.

Chemokine, C motif, Ligand 2 (XCL2): Also known as small inducible cytokine subfamily C, member 2 (SCYC2) and single cysteine motif 1B (SCM1B), XCL2 is a cytokine that is predominantly expressed in activated T cells and induces chemotaxis of cells that express the chemokine receptor 1 (XCR1). XCL2 nucleic acid molecules and proteins are included. XCL2 sequences are publicly available. For example, GENBANK® Accession Nos. BC070308.1 and EAW90827.1 disclose exemplary human XCL2 nucleotide and protein sequences, respectively (incorporated herein by reference as present in GENBANK® on Oct. 20, 2017). One of ordinary skill in the art can identify additional XCL2 nucleic acid and protein sequences, including XCL2 variants that retain XCL2 biological activity (such as increased production with T cell activation).

Chemokine (C—C Motif) ligand 3 (CCL3): Also known as small inducible cytokine A3 (SCYA3; e.g., OMIM 182283), macrophage inflammatory protein 1-α (MIP1α), and tonsillar lymphocyte LD78 α Protein (LD78-α), CCL3 is a monokine involved in the acute inflammatory state of polymorphonuclear leukocyte recruitment and activation. CCL3 is expressed in many cell types, but most notably macrophages, dendritic cells, and lymphocytes. Further, CCL3 plays an important role in inflammation and the immune response to infection and can promote homeostasis. CCL3 has been associated with such diseases as HIV and rheumatoid arthritis. CCL3 nucleic acid molecules and proteins are included. CCL3 sequences are publicly available. For example, GenBank® Accession Nos. NM_002983.2, NM_013025.2, and NM_011337.2, disclose exemplary human, rat, and mouse CCL3 nucleotide sequences, respectively, and GenBank® Accession Nos. NP_002974.1, EDM05492.1, and NP_035467.1 disclose exemplary human, rat, and mouse CCL3 protein sequences, respectively (all of which are incorporated herein by reference as present in GENBANK® on Oct. 20, 2017). One of ordinary skill in the art can identify additional CCL3 nucleic acid and protein sequences, including CCL3 variants that retain CCL3 biological activity (such as increased production with T cell activation).

Cluster of Differentiation 28 (CD28): Also known as antigen CD28, T cell antigen CD28, and Tp44 (e.g., OMIM 186760), CD28 is expressed on T cells and provides co-stimulatory signals required for T cell activation and survival. CD28 plays a role in stimulating interleukin production through T cell stimulation, serves as a receptor for cluster of differentiation (CD) 80 and CD86, and is the only B7 receptor constitutively expressed on naive T cells. CD28 nucleic acid molecules and proteins are included. CD28 sequences are publicly available. For example, GENBANK® Accession Nos. NM_006139.3, X55288.1, and NM_007642.4, disclose exemplary human, rat, and mouse CD28 nucleotide sequences, respectively, and GenBank® Accession Nos. AAL40931.1, CAA39003.1, and EDL00156.1 disclose exemplary human, rat, and mouse CD28 protein sequences, respectively (all of which are incorporated herein by reference as present in GENBANK® on Oct. 20, 2017). One of ordinary skill in the art can identify additional CD28 nucleic acid and protein sequences, including CD28 variants that retain CD28 biological activity (such as stimulating T cell activation).

Complementarity and percentage complementarity: Molecules with complementary nucleic acids form a stable duplex or triplex when the strands bind, (hybridize), to each other by forming Watson-Crick, Hoogsteen or reverse Hoogsteen base pairs. Stable binding occurs when an oligonucleotide remains detectably bound to a target nucleic acid sequence under the required conditions.

Complementarity is the degree to which bases in one nucleic acid strand base pair with the bases in a second nucleic acid strand. Complementarity is conveniently described by percentage, e.g., the proportion of nucleotides that form base pairs between two strands or within a specific region or domain of two strands. For example, if 10 nucleotides of a 15-nucleotide oligonucleotide form base pairs with a targeted region of a DNA molecule, that oligonucleotide is said to have 66.67% complementarity to the region of DNA targeted.

In the present disclosure, "sufficient complementarity" means that a sufficient number of base pairs exist between the oligonucleotide and the target sequence to achieve detectable binding. When expressed or measured by percentage of base pairs formed, the percentage complementarity that fulfills this goal can range from as little as about 50% complementarity to full (100%) complementarity. In general, sufficient complementarity is at least about 50%, about 75% complementarity, about 90% or 95% complementarity, and or about 98% or even 100% complementarity.

A thorough treatment of the qualitative and quantitative considerations involved in establishing binding conditions that allow one skilled in the art to design appropriate oligonucleotides for use under the desired conditions is provided by Beltz et al. *Methods Enzymol* 100:266-285, 1983, and by Sambrook et al. (ed.), *Molecular Cloning: A Laboratory Manual,* 2nd ed., vol. 1-3, Cold Spring Harbor Laboratory Press, Cold Spring Harbor, N.Y., 1989.

Concanavalin A (ConA): A lectin (carbohydrate-binding protein) from the jack-bean, *Canavalia ensiformis*. It binds to mainly internal and non-reducing terminal α-D-mannosyl and α-D-glucosyl groups. ConA binds to surfaces of many cell types and is widely used in biology and biochemistry to characterize glycoproteins and other sugar-containing molecules on the surface of cells. It is also used to purify glycoproteins by affinity chromatography. ConA sequences are publicly available. GENBANK® Accession Nos. AAL09432.1 and AF308777.1, incorporated herein by reference as available on Oct. 20, 2017, provide exemplary jack bean ConA protein and nucleotide sequences, respectively. One of ordinary skill in the art can identify additional ConA nucleic acid and protein sequences, including ConA variants that retain ConA biological activity (such as T cell activation).

Contacting: Placement in direct physical association, including for example, a solid or liquid form. Contacting can occur in vitro with isolated cells or tissue or in vivo by administering to a subject (for example, administering a compound to a subject to achieve a desired effect and/or a desired concentration for a desired time at a target cell type in the body, for example, T cells).

Control: A "control" refers to a sample or standard used for comparison with an experimental sample. In some embodiments, the control is a sample obtained from a healthy patient. In other embodiments, the control is an activated T cell that has not been contacted with a miRNA or a miRNA inhibitor, such as those disclosed herein. In other embodiments, the control is a historical control or standard reference value or range of values (such as a previously tested control sample, such as a measure of T cell activation that represents baseline or normal values, such as a measure of T cell activation in a population or group, such as individuals with a particular condition or disorder).

A difference between the value of a parameter measured in a test sample and a control can be an increase or a decrease. The difference can be a qualitative difference or a quantitative difference, for example a statistically significant difference. In some examples, a difference is an increase or decrease, relative to a control, of at least about 5%, such as at least about 10%, at least about 20%, at least about 30%, at least about 40%, at least about 50%, at least about 60%, at least about 70%, at least about 80%, at least about 90%, at least about 100%, at least about 150%, at least about 200%, at least about 250%, at least about 300%, at least about 350%, at least about 400%, at least about 500%, or greater than 500%.

Cytokine storm: Also known as cytokine cascade and hypercytokinemia, a cytokine storm is a potentially fatal immune reaction consisting of a positive feedback loop between cytokines and white blood cells, with highly elevated levels of various cytokines.

Cytokines: Proteins made by cells that affect the behavior of other cells, such as lymphocytes. In one embodiment, a cytokine is a chemokine, a molecule that affects cellular trafficking, such as C—C motif chemokine ligand 3 (CCL3) and XC chemokine ligand 2 (XCL2). The term "cytokine" is used as a generic name for a diverse group of soluble proteins and peptides that act as humoral regulators and modulate the functional activities of individual cells and tissues under normal or pathological conditions. These proteins also mediate interactions between cells directly and regulate processes taking place in the extracellular environment. Examples of cytokines include, but are not limited to, tumor necrosis factor α (TNFα), interleukin-2 (IL-2), interleukin-4 (IL-4), interleukin-6 (IL-6), interleukin-10 (IL-10), interleukin-17 (IL-17), interleukin-12 (IL-12), interleukin-21 (IL-21), macrophage inflammatory protein 2 (MIP-2), keratinocyte derived cytokine (KC), interferon-γ (INF-γ), and granulocyte-macrophage colony-stimulating factor (GM-CSF).

Effective amount: A quantity of an agent or compound sufficient to achieve a desired effect in a subject or a cell being treated. For instance, this can be an amount sufficient to increase or decrease T cell activation. The effective amount of the agent will depend on several factors, including, but not limited to, the subject or cells being treated and the manner of administration of the therapeutic composition. In some instances, a "therapeutically effective amount" is a quantity of an agent or compound sufficient to prevent advancement, delay progression, or to cause regression of a disease or condition, or which is capable of reducing symptoms caused by a disease, such as an inflammatory or autoimmune disease or disorder.

Expression: The conversion of the information encoded in a gene (such as a T cell activation-related gene) into microRNA, messenger RNA, and/or the conversion of mRNA into a protein. "Differential expression" or "altered expression" is a difference, such as an increase or decrease, in the conversion of such gene-encoded information. In some examples, the difference is relative to a control or reference value. Detecting differential expression can include measuring a change in nucleic acid or protein expression, such as a change in expression of one or more T cell activation-related miRNAs disclosed herein.

Expression vector: A vector that includes a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes), and viruses (e.g., lentiviruses, retroviruses, adenoviruses, and adeno-associated viruses) that incorporate the recombinant polynucleotide.

Granulocyte-Macrophage Colony Stimulating Factor (GM-CSF): Also known as granulocyte-macrophage colony stimulating factor 2 (GM-CSF2; e.g., OMIM 138960), GM-CSF is a glycoprotein cytokine secreted by various cell types involved in immune function (e.g., T cells) and plays a role in the immune/inflammatory cascade. GM-CSF nucleic acid molecules and proteins are included. GM-CSF sequences are publicly available. For example, GENBANK® Accession Nos. M11220.1, U00620.1, and AH003766.2 disclose exemplary human, rat, and mouse GM-CSF nucleotide sequences, respectively, and GENBANK® Accession Nos. AAA52578.1, NP_446304.1, and CAA26820.1 disclose exemplary human, rat, and mouse GM-CSF protein sequences, respectively (all of which are incorporated herein by reference as present in GENBANK® on Oct. 20, 2017). One of ordinary skill in the art can identify additional GM-CSF nucleic acid and protein sequences, including GM-CSF variants that retain GM-CSF biological activity (such as increased production with T cell activation).

Immune system disorder: A disease or disorder that is associated with a pathological immune response in a subject (see Intl. Patent Pub. No. WO 2013/192294 and U.S. Patent Pub. No. 2011/00811323, both of which are incorporated herein by reference). Examples include immunodeficiency (e.g., primary or hereditary immunodeficiency and immunodeficiencies associated with other conditions, such as immunosuppression associated with, for example, HIV, old age, and cancer), cytokine storm, allergies, asthma, various types of inflammation, and autoimmune disorders.

Immunocompromised: An immunocompromised subject is a subject who is incapable of developing or unlikely to develop a robust immune response, usually as a result of disease, malnutrition, or immunosuppressive therapy. An immunocompromised immune system is an immune system that is functioning below normal. Immunocompromised subjects are more susceptible to opportunistic infections, for example viral, fungal, protozoan, or bacterial infections, prion diseases, and certain neoplasms. Those who can be considered to be immunocompromised include, but are not limited to, subjects with AIDS (or HIV positive), subjects with severe combined immune deficiency (SCID), diabetics, subjects who have had transplants and who are taking immunosuppressives, and those who are receiving chemotherapy for cancer. Immunocompromised individuals also include subjects with most forms of cancer (other than skin cancer), sickle cell anemia, cystic fibrosis, those who do not have a spleen, subjects with end stage kidney disease (dialysis), and those who have been taking corticosteroids on a frequent basis by pill or injection within the last year. Subjects with severe liver, lung, or heart disease also may be immunocompromised.

Inflammatory disease or disorder: A primary inflammation disorder is a disorder that is caused by inflammation itself. A secondary inflammation disorder is inflammation that is the result of another disorder. Inflammation can lead to inflammatory diseases or disorders, such as rheumatoid arthritis, osteoarthritis, inflammatory lung disease (including chronic obstructive pulmonary lung disease), inflammatory bowel disease (including ulcerative colitis and Crohn's Disease), periodontal disease, polymyalgia rheumatica, atherosclerosis, systemic lupus erythematosus, systemic sclerosis, Sjogren's Syndrome, asthma, allergic rhinitis, and skin disorders (including dermatomyositis and psoriasis) and the like.

Inflammation is a localized protective response elicited by injury to tissue that serves to sequester the inflammatory agent. Inflammation is orchestrated by a complex biological response of vascular tissues to harmful stimuli, such as pathogens, damaged cells, or irritants. It is a protective attempt by the organism to remove the injurious stimuli as well as initiate the healing process for the tissue. An inflammatory response is characterized by an accumulation of white blood cells, either systemically or locally at the site of inflammation. The inflammatory response may be measured by many methods, including, but not limited to measuring the number of white blood cells, the number of polymorphonuclear neutrophils (PMN), a measure of the degree of PMN activation, such as luminol enhanced-chemiluminescence, or a measure of the amount of cytokines present. C-reactive protein is a marker of a systemic inflammatory response.

Inhibiting or treating a disease: Inhibiting the full development of a disease or condition, for example, in a subject who is at risk for a disease. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology.

Interferon gamma (IFNγ): Also known as IFNG, IFG, IFN immune (IFI; e.g., OMIM 147570), IFNγ is a cytokine that binds the IFNγ receptor (IFNγR) and exhibits antiviral, antibacterial, and antiprotozoan activity. IFNγ is primarily expressed by leukocytes, such as T cells. IFNγ sequences are publicly available. For example, GENBANK® Accession Nos. AAB59534.1, AAA41362.1, and ACR22511.1, incorporated by reference herein, disclose exemplary human, rat, and mouse IFNγ protein sequences, and GENBANK® Accession Nos. NM_000619.2, NM_138880.2, and NM_008337.4, incorporated by reference herein, disclose exemplary human, rat, and mouse IFNγ nucleotide sequences, respectively (all of which are incorporated herein by reference as present in GENBANK® on Oct. 20, 2017). One of ordinary skill in the art can identify additional IFNγ nucleic acid and protein sequences, including IFNγ variants that retain IFNγ biological activity (such as increased production with T cell activation).

Interleukin 2 (IL-2): Also known as T cell growth factor (TCGF; e.g., OMIM 147680), IL-2 is a cytokine involved in the immune system. Through binding IL-2 receptors, IL-2 plays a role in regulating white blood cell (WBC) activities, responding to microbial infection, and discriminating between endogenous and exogenous molecules. IL-2 nucleic acid molecules and proteins are included. IL-2 sequences are publicly available. For example, GENBANK® Accession Nos. S77834.1, NM_053836.1, and NM_008366.3 disclose exemplary human, rat, and mouse IL-2 nucleotide sequences, respectively, and GENBANK® Accession Nos. AAB46883.1, NP_446288.1, and NP_032392.1 disclose exemplary human, rat, and mouse IL-2 protein sequences, respectively (all of which are incorporated herein by reference as present in GENBANK® on Oct. 20, 2017). One of ordinary skill in the art can identify additional IL-2 nucleic acid and protein sequences, including IL-2 variants that retain IL-2 biological activity (such as increased production with T cell activation).

Interleukin 4 (IL-4): Also known as B-cell stimulatory factor (BSF1; e.g., OMIM 147780), IL-4 is a cytokine that binds the IL-4 receptor (IL-4Ra) and plays a role in regulating immunity. IL-4 can induce differentiation and proliferation of leukocytes, such as B and T cells. IL-4 is closely related and has functions similar to IL-13. IL-4 sequences are publicly available. For example, GENBANK® Accession Nos. CAP72493.1, AAR87867.1, and AAH27514.1, incorporated by reference herein, disclose exemplary human, rat, and mouse IL-4 protein sequences, and M13982.1, NM_201270.1, and M25892.1 disclose exemplary human, rat, and mouse IL-4 nucleotide sequence, respectively (all of which are incorporated herein by reference as present in GENBANK® on Oct. 20, 2017). One of ordinary skill in the art can identify additional IL-4 nucleic acid and protein sequences, including IL-4 variants that retain IL-4 biological activity (such as increased production with T cell activation).

Interleukin 6 (IL-6): Also known as interferon beta-2; IFNB2, B-cell differentiation factor, B-cell stimulatory factor 2 (BSF2), hepatocyte stimulatory factor (HSF), and hybridoma growth factor (HGF; e.g., OMIM 147620), IL-6 is an interleukin that acts as both a proinflammatory cytokine and an anti-inflammatory myokine. IL-6 is secreted by T cells and macrophages to stimulate immune response (e.g., during infection and after trauma, especially burns or other tissue damage leading to inflammation) and has been implicated in the inflammatory and autoimmune processes of various diseases. Exemplary protein and nucleotide sequences for IL-6 are available at GENBANK® (e.g., Accession Nos. P05231.1 and NM_001318095.1, respectively, both of which are incorporated by reference herein as available on Oct. 20, 2017). One of ordinary skill in the art can identify additional IL-6 nucleic acid and protein sequences, including IL-6 variants that retain IL-6 biological activity (such as increased production with T cell activation).

Interleukin 17A (IL-17A or IL-17): Also known as cytotoxic T-lymphocyte-associated serine esterase 8 (CTLA8; e.g., OMIM 603149), IL-17A is a proinflammatory cytokine primarily secreted by activated T cells. IL-17 simulates a variety of cells to produce inflammatory mediators, including IL-1, TNFα, and chemokines, ultimately leading to neutrophil and leukocyte recruitment, the hallmark of inflammatory disease. Includes IL-17A nucleic acid molecules and proteins. IL-17A sequences are publicly available. For example, GENBANK® Accession Nos. NM_002190.2, NM_001106897.1, and NM_010552.3 disclose exemplary human, rat, and mouse IL-17A nucleotide sequences, respectively, and GENBANK® Accession Nos. AAH67505.1, NP_001100367.1, and NP_034682.1 disclose exemplary human, rat, and mouse IL-17A protein sequences, respectively (all of which are incorporated herein by reference as present in GENBANK® on Oct. 20, 2017). One of ordinary skill in the art can identify additional IL-17A nucleic acid and protein sequences, including IL-17A variants that retain IL-17A biological activity (such as increased production with T cell activation).

Isolated: An "isolated" biological component (such as a nucleic acid molecule, protein, or cell) has been substantially separated or purified away from other biological components in the cell of the organism or from the organism in which the component naturally occurs, such as other chromosomal and extra-chromosomal DNA and RNA, proteins, and cells. Nucleic acid molecules and proteins that have been "isolated" include T cell activation-related molecules (such as miRNA) and proteins purified by standard purification methods. The term also embraces nucleic acid molecules, proteins, and peptides prepared by recombinant expression in a host cell as well as chemically synthesized nucleic acid molecules and proteins. For example, an isolated miRNA molecule is one that is substantially separated from other types of nucleic acids in a cell.

Label: An agent capable of detection, for example by immunohistochemistry, spectrophotometry, flow cytometry, or microscopy. For example, a label can be attached to a nucleic acid molecule, thereby permitting detection of the nucleic acid molecule or protein. For example, a biotin and/or fluorescent label can be attached to an miRNA molecule for detection. Examples of labels include, but are not limited to, fluorophores; radioactive or heavy, stable isotopes; enzyme substrates; co-factors; ligands; chemiluminescent agents; haptens; enzymes; and combinations thereof. Methods for labeling and guidance in the choice of labels appropriate for various purposes are discussed for example in Sambrook et al. (Molecular Cloning: A Laboratory Manual, Cold Spring Harbor, N.Y., 1989) and Ausubel et al. (In Current Protocols in Molecular Biology, John Wiley & Sons, New York, 1998).

Microarray: A microscopic, ordered array of nucleic acids (such as microRNAs), proteins, small molecules, cells, or other substances that enables parallel analysis of biochemical samples. A nucleic acid microarray consists of different nucleic acid probes, known as capture probes that are chemically attached to a solid substrate, which can be a microchip, a glass slide, or a microsphere-sized bead. Microarrays can be used, for example, to measure the expression levels of large numbers of microRNAs simultaneously.

Microgravity: A state in which there is very little net gravitational force, for example, gravity less than about 0.1×g. Microgravity conditions exist in space, for example, aboard the Space Shuttle, the International Space Station, a satellite, or a rocket while in flight outside the Earth's atmosphere. Simulated microgravity is microgravity which is simulated by a set of Earth-based conditions that mimic microgravity, such as by balancing gravity with equal and opposite forces (for example, shear force, centripetal force, Coriolus forces, buoyancy, and/or magnetic field). In one example, simulated microgravity may be generated by use of a clinostat, such as a rotating wall vessel (RWV). In another example, simulated microgravity may be generated by a random positioning machine (RPM). The terms "microgravity conditions" and "microgravity" are used synonymously herein. Normal gravity is the gravity normally experienced on Earth, such as on the surface of the Earth and/or in its atmosphere (for example, in aircraft in the atmosphere of the Earth). Gravity is measured in terms of acceleration due to gravity, denoted by g. The strength (or apparent strength) of Earth's gravity varies with latitude, altitude, local topography, and geology. In some examples, normal gravity (such as 1×g) is about 9-10 m/s$^2$, for example, about 9.7-9.9 m/s$^2$. In particular preferred embodiments, normal gravity is that experienced on the surface of the Earth under normal gravity at that location on the Earth.

MicroRNA (miRNA, miR): Single-stranded RNA molecules that regulate gene expression. MicroRNAs are generally 20-25 nucleotides in length. MicroRNAs are processed from primary transcripts known as pri-miRNA to short stem-loop structures called precursor (pre)-miRNA and finally to functional, mature microRNA. Mature microRNA molecules are partially complementary to one or more messenger RNA molecules, and their primary function is to down-regulate gene expression. MicroRNAs regulate gene expression through the RNAi pathway.

MicroRNA can be used therapeutically (e.g., miRNA therapy) by inhibiting and/or expressing certain microRNA. Methods of inhibiting and expressing miRNA are known, such as the methods of Christopher et al., Perspect Clin Res., 7(2): 68-74, 2016, and Baumann and Winkler, Future Med Chem., 6(17): 1967-1984, 2014, both of which are incorporated herein by reference. Such methods include inhibition of microRNA by microRNA antagonists (e.g., antisense nucleotides) and microRNA replacement, such as with microRNA and/or microRNA mimics.

An miRNA mimic or an miRNA inhibitor mimic includes an miRNA or miRNA inhibitor that has the same sequence as the native or wild type miRNA, but has a modified backbone, a modified base, and/or a 5' or 3' end modification. In some examples an miRNA mimic or an miRNA inhibitor mimic may be less susceptible to degradation or nuclease activity. An miRNA mimic or an miRNA inhibitor mimic is an miRNA or miRNA inhibitor with at least one sequence modification and having 75% or higher sequence identity to a native or wild type miRNA or miRNA inhibitor and that also binds to the same mRNA(s) with similar affinity as the wild type or native miRNA. The disclosed miRNA or miRNA inhibitors may include one or more than one modification, for example, an miRNA with at least one sequence modification (e.g., 75% or higher sequence identity to a wild type miRNA), and also having a modified backbone, base, and/or end modification.

MicroRNA sequences are publicly available. For example, miRBase (mirbase.org) includes a searchable database of annotated miRNA sequences. miRNA sequences are also available through other databases known to one of ordinary skill in the art, including the National Center for Biotechnology Information (ncbi.nlm.nih.gov). One of ordinary skill in the art can also identify targets for specific miRNAs utilizing public databases and algorithms, for example at MicroCosm Targets (ebi.ac.uk/enright-srv/microcosm/htdocs/targets/), TargetScan (targetscan.org), and PicTar (pictar.mdc-berlin.de).

Pharmaceutically acceptable carrier: The pharmaceutically acceptable carriers (vehicles) useful in this disclosure are conventional. *Remington: The Science and Practice of Pharmacy*, The University of the Sciences in Philadelphia, Editor, Lippincott, Williams, & Wilkins, Philadelphia, Pa., 21$^{st}$ Edition (2005), describes compositions and formulations suitable for pharmaceutical delivery of one or more therapeutic compounds, molecules or agents.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Additional pharmaceutical compositions may include vectors (in which the miRNA or miRNA inhibitor is included), lipid-based delivery systems (such as liposomes), exosomes, or nanoparticles (such as PLGA nanoparticles). In other examples, the disclosed miRNAs or miRNA inhibitors (or mimics thereof) may be delivered by carriers or modification links.

Sample: A biological specimen containing genomic DNA, RNA (e.g., miRNA), protein, or combinations thereof, obtained from a subject. Examples include, but are not limited to, peripheral blood, serum, plasma, urine, saliva, tissue biopsy, fine needle aspirate, surgical specimen, and autopsy material. In one example, a sample is a blood sample from a subject with or at risk for an immune system disorder. In some examples, samples are used directly in the methods provided herein. In some examples, samples are manipulated prior to analysis using the disclosed methods, such as through concentrating, filtering, centrifuging, diluting, desalting, denaturing, reducing, alkylating, proteolyzing, or combinations thereof. In some examples, components of the samples are isolated or purified prior to analysis using the disclosed methods, such as isolating cells, proteins, and/or nucleic acid molecules from the samples.

Subject: Living multi-cellular vertebrate organisms, a category that includes both human and non-human mammals. Subjects include veterinary subjects, including livestock such as cows and sheep, rodents (such as mice and rats), and non-human primates. In a particular example, a subject is one who has or is at risk for an immune system disorder (e.g., an inflammatory or autoimmune disease). In a particular example, a subject is one who is suspected of having for an immune system disorder (e.g., an inflammatory or autoimmune disease).

T Cell: A white blood cell critical to the immune response. T cells include, but are not limited to, $CD4^+$ T cells and $CD8^+$ T cells. A $CD4^+$ T lymphocyte is an immune cell that carries a marker on its surface known as "cluster of differentiation 4" (CD4). These cells, also known as helper T cells, help orchestrate the immune response, including antibody responses as well as killer T cell responses. $CD8^+$ T cells carry the "cluster of differentiation 8" (CD8) marker. In one embodiment, a CD8 T cell is a cytotoxic T lymphocyte. In another embodiment, a CD8 cell is a suppressor T cell.

As used herein, "allogeneic" encompasses a genetically different phenotype present in non-identical individuals of the same species. Cells, tissues, organs, and the like from, or derived from, a non-identical individual of the same species are "allogeneic." An "alloantigen" encompasses any antigen recognized by different individuals of the same species. Organisms, cells, tissues, organs, and the like from, or derived from, a single individual, or from a genetically identical individual are "autologous."

T cell activation: To initiate or increase the action or function of a T cell. T cells are activated by binding of an antigen (such as an antigen bound to an MHC molecule, for example, on an antigen presenting cell or infected cell) to a T cell receptor on the cell surface. Activation of a T cell also requires a co-stimulatory signal in addition to T cell receptor signaling. In some examples, the co-stimulatory signal is provided by CD28. In particular examples, activation of a T cell is detected by an increase in cell proliferation and/or expression or secretion of a cytokine (such as IL-2, IL-4, IL-6, IFNγ, or TNFα) as compared to a control. In some examples, activation of a CD8+ T cell is detected by an increase in cytolytic activity as compared to a control.

Some miRNA are related to T cell activation ("T cell activation-related miRNA"). T cell activation-related miRNA can exhibit differential expression (e.g., increased or decreased expression) under conditions of underactive or overactive T cell activation (e.g., in a subject that has an immunodeficiency and/or an inflammatory or autoimmune disorder). Non-limiting examples of T cell activation-related miRNA include mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p.

Tumor necrosis factor α (TNFα): Tumor necrosis factor (TNF, tumor necrosis factor α, TNFα, cachexin, or cachectin) is a cell signaling protein (cytokine) involved in systemic inflammation and is one of the cytokines that make up the acute phase reaction. It is produced chiefly by activated macrophages, although it can be produced by many other cell types, such as CD4+ lymphocytes, NK cells, neutrophils, mast cells, eosinophils, and neurons. Exemplary protein and nucleotide sequences for TNFα are available at GENBANK® (e.g., Accession Nos. P01375.1 and NM_001199054.1, respectively, both of which are incorporated by reference herein as available on Oct. 20, 2017). One of ordinary skill in the art can identify additional TNFα nucleic acid and protein sequences, including TNFα variants that retain TNFα biological activity (such as increased production with T cell activation).

Vector: A vector may include nucleic acid sequences that permit it to replicate in a host cell, such as an origin of replication. A vector may also include one or more nucleic acids of interest (such as a microRNA or miRNA inhibitor nucleic acid) and/or selectable marker genes and other genetic elements known in the art. A vector can transduce, transform, or infect a cell, thereby causing the cell to express nucleic acids and/or proteins (which may not be native to the cell). A vector optionally includes materials to aid in achieving entry of the nucleic acid into the cell, such as a viral particle, liposome, protein coating or the like. A vector can be a viral vector.

Overview

Disclosed herein are methods for treating an immune system condition in a subject (such as a human subject). The methods can include measuring expression of at least one T cell activation-related miRNA in a sample (e.g., a biological sample, tissue sample, or biological fluid sample, such as a blood sample, including plasma, whole blood, serum, or dried blood spots) obtained from a subject. The at least one T cell activation-related miRNA can include at least one of mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p. The methods include measuring differential expression of the at least one T cell activation-related miRNA compared to a control (such as a control representing expression of the at least one T cell activation-related miRNA in a subject or a population who does not have an immune system condition). The methods also include administering at least one of miRNA therapy, other immunomodulatory therapy, non-steroidal anti-inflammatory drugs (NSAIDs), acetaminophen, corticosteroids, anti-inflammatory supplements, biologics, disease-modifying antirheumatic drugs (DMARDs), antimalarial drugs, stem cell or blood transfusion, physical therapy, and/or surgery, thereby treating the subject.

Also disclosed herein are methods for diagnosing an immune system condition in a subject (such as a human subject). In some examples, the methods include measuring expression of at least one T cell activation-related miRNA in a sample (e.g., a biological sample, tissue sample, or biological fluid sample, such as a blood sample, including plasma, whole blood, serum, or dried blood spots) obtained from a subject. The at least one T cell activation-related miRNA includes at least one of mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p. The methods also include comparing the expression of the at least one T cell activation-related miRNA with a control (such as a control representing expression of the at least one T cell activation-related miRNA in a subject or a population who does not have an immune system condition) and determining that the subject has an immune system condition when differential expression of the T cell activation-related miRNA compared to the control is detected. In particular examples, the at least one T cell activation-related miRNA includes at least one of miR-7-1-3p, miR-128-3p, miR-26b-5p, miR-125b-5p, and/or miR-363-3p.

Measuring the expression of at least one T cell activation-related miRNA includes performing a microarray analysis, a polymerase chain reaction (PCR) analysis, and/or an immunohistochemistry analysis of the sample obtained from the subject. In specific, non-limiting examples, the expression is measured using a microarray analysis. In other non-limiting examples, the microarray analysis includes labeling the at least one T cell activation-related miRNA using a detectable label, such as a fluorescent label, biotin, a radiolabel, an enzyme, a luminescent label, and/or a colorimetric label. In particular examples, the detectable label is a fluorescent label. In other particular examples, miRNA therapy is administered, such as administering miRNA or an inhibitor of miRNA or T cells contacted with miRNA or an inhibitor of miRNA.

Further disclosed herein are methods for treating an immune system condition in a subject (such as a human subject). In some examples, the methods can include selecting a subject with an immune system condition. In specific examples, the immune system condition can be an underactive or an overactive immune response. The methods further includes administering to the subject a therapeutically effective amount of miRNA (such as human miRNA and/or an miRNA mimic) and/or an inhibitor of miRNA, thereby treating the immune system condition. In specific, non-limiting examples, where the immune system condition includes an underactive immune response, the miRNA can include at least one of mir-326, mir-6860, miR-6860, mir-1976, mir-550b-1, mir-550b-2, miR-8071, miR-4481, and/or mir-3689b and/or the inhibitor of miRNA can include an inhibitor of at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p. In other examples, where the immune system condition includes an overactive immune response, the an inhibitor of miRNA can include an inhibitor of at least one of mir-326, mir-6860, miR-6860, mir-1976, mir-550b-1, mir-550b-2, miR-8071, miR-4481, and/or mir-3689b and/or the miRNA includes at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p.

Additionally, disclosed herein are methods for treating an immune system condition in a subject (such as a human subject). In some examples, the methods can include selecting a subject with an immune system condition. In specific examples, the immune system condition can include an underactive or overactive immune response. In specific, non-limiting examples, where the immune system condition includes an underactive immune response, the methods can include activating T cells and contacting the activated T cells with an effective amount of miRNA (such as human miRNA and/or an miRNA mimic), including at least one of mir-326, mir-6860, miR-6860, mir-1976, mir-550b-1, mir-550b-2, miR-8071, miR-4481, and/or mir-3689b, or a mimic thereof, and/or an inhibitor of miRNA, including an inhibitor of at least one of miR-25-3p, miR-629-3p, miR-330-3p, miR-501-3p, miR-7-1-3p, miR-128-3p, miR-26b-5p, miR-125b-

5p, miR-99a-5p, and/or miR-363-3p, or a mimic thereof, thereby treating the immune system condition. In other non-limiting examples, where the immune system condition includes an overactive immune response, the methods can include contacting activated T cells with an effective amount of an inhibitor of miRNA, including an inhibitor of at least one of mir-326, mir-6860, miR-6860, mir-1976, mir-550b-1, mir-550b-2, miR-8071, miR-4481, and/or mir-3689b, or a mimic thereof and/or miRNA (such as human miRNA and/or an miRNA mimic), including at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby treating the immune system condition.

Also disclosed herein are methods for altering (e.g., increasing or decreasing) T cell activation in a subject (such as a human subject). In some examples, the methods can include selecting a subject with activated T cells. In specific, non-limiting examples, the methods can include administering to the subject a therapeutically effective amount of miRNA (such as human miRNA and/or an miRNA mimic), including at least one of mir-326, mir-6860, miR-6860, mir-1976, mir-550b-1, mir-550b-2, miR-8071, miR-4481, and/or mir-3689b, or a mimic thereof, and/or an inhibitor of miRNA, including an inhibitor of at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby increasing T cell activation as compared to a control. In other non-limiting examples, the methods can include administering to the subject a therapeutically effective amount of an inhibitor of miRNA, including an inhibitor of at least one of mir-326, mir-6860, miR-6860, mir-1976, mir-550b-1, mir-550b-2, miR-8071, miR-4481, and/or mir-3689b, or a mimic thereof and/or miRNA (such as human miRNA and/or an miRNA mimic), including at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby decreasing T cell activation as compared to a control.

Further disclosed herein are methods for altering (e.g., increasing or decreasing) T cell activation in a subject (such as a human subject). In some examples, the methods can include activating T cells and contacting the activated T cells with an effective amount miRNA (such as human miRNA and/or an miRNA mimic), including at least one of mir-326, mir-6860, miR-6860, mir-1976, mir-550b-1, mir-550b-2, miR-8071, miR-4481, and/or mir-3689b, or a mimic thereof and/or an inhibitor of miRNA, including an inhibitor of at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby increasing T cell activation as compared to a control. In other examples, the methods include contacting activated T cells with an effective amount of an inhibitor of miRNA, including an inhibitor of at least one of mir-326, mir-6860, miR-6860, mir-1976, mir-550b-1, mir-550b-2, miR-8071, miR-4481, and/or mir-3689b, or a mimic thereof, and/or miRNA (such as human miRNA and/or an miRNA mimic), including at least one of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby decreasing the T cell activation as compared to a control.

In specific examples, activating T cells includes increasing T cell proliferation, T cell cytokine production, T cell chemokine production, or a combination of two or more thereof. For example, the cytokine can include interleukin (IL)-2, IL-4, IL-6, IL-17, tumor necrosis factor (TNF)-α, interferon (IFN)-γ, granulocyte-macrophage colony stimulating factor, or a combination of two or more thereof and/or the chemokine comprises CCL3, XCL2, or a combination thereof. In further examples, the T cell can be a CD4+ T cell, a CD8+ T cell, or a combination thereof. In other examples, activating T cells can include contacting the T cells with CD28 and Concanavalin A.

In particular examples, activating T cells and/or contacting the activated T cells with an effective amount of the miRNA or the inhibitor of miRNA is performed in vitro. In some examples, the activated T cells are administered to a subject after the activated T cells are contacted with miRNA or an inhibitor of miRNA. In other examples, the miRNA inhibitor includes a nucleic acid at least 90% complementary to a mature miRNA. In further examples, the miRNA can be a pri-miRNA, a pre-miRNA, or a mature miRNA.

In still further examples, the methods disclosed herein can include a subject that is infected with human immunodeficiency virus, a subject that has been or will be exposed to microgravity, a subject experiencing a cytokine storm, or a subject with an inflammatory or autoimmune disorder. In specific, non-limiting examples, the inflammatory disorder can include rheumatoid arthritis, chronic obstructive pulmonary lung disease, inflammatory bowel disease, or systemic lupus erythematosus. In other non-limiting examples, the autoimmune disorder can include multiple sclerosis, ankylosing spondylitis, celiac disease, Crohn's disease, Graves' disease, Hashimoto thyroiditis, or autoimmune uveitis.

MicroRNAs

The miRNAs of use in the disclosed methods include miRNAs which are differentially regulated in activated T cells that have been exposed to microgravity as compared to activated T cells that have not been exposed to microgravity. In some examples, the T cells are exposed to microgravity (either in vivo or in vitro) and are activated in microgravity conditions. In other examples, the T cells are exposed to microgravity (either in vivo or in vitro) and are activated upon return to normal gravity.

MicroRNAs of use in the disclosed methods include the miRNAs provided in Table 1, below. In some examples, the miRNAs are miR-25-3p, miR-629-3p, miR-330-3p, miR-501-3p, miR-7-1-3p, miR-128-3p, miR-26b-5p, miR-125b-5p, miR-99a-5p, miR-363-3p, mir-326, mir-6860, miR-6860, mir-1976, mir-550b-1, mir-550b-2, miR-8071, miR-4481, and mir-3689b. In some examples, the miRNA is a mouse miRNA or a human miRNA. miRNA sequences are publicly available. In some examples, the miRNAs include those with the miRBase Accession numbers listed in Table 1. One of ordinary skill in the art can identify the sequences of the listed miRNAs, or other miRNAs (such as those listed in Table 1), for example using publicly available databases such as the National Center for Biotechnology Information (ncbi.nlm.nih.gov) and miRBase (mirbase.org).

TABLE 1

Exemplary miRNAs and Accession Numbers

| miRNA | miRNA Sequence | miRBase Accession Numbers |
|---|---|---|
| miR-25-3p | CAUUGCACUUGUCUCGGUCUGA (SEQ ID NO: 1) | MIMAT0000081 |
| mir-326 | CUCAUCUGUCUGUUGGGCUGGAGGCAGGGCCUUUGUG AAGGCGGGUGGUGCUCAGAUCGCCUCUGGGCCCUUCC UCCAGCCCCGAGGCGGAUUCA (SEQ ID NO: 2); CUCAUCUGUCUGUUGGGCUGGGGGCAGGGCCUUUGUG AAGGCGGGUUAUGCUCAGAUCGCCUCUGGGCCCUUCC UCCAGUCCCGAGGCAGAUUUA (SEQ ID NO: 3) | MI0000808; MI0000598 |
| mir-6860 | GUUAAGCAUUGGGGAGUUUGGAGUCGGUGGGUGGAG CCAAACUGGGCAGGGCUGUGGUGAGUGAGU (SEQ ID NO: 4); ACUGGGCAGGGCUGUGGUGAGU (SEQ ID NO: 5) | MI0022707; MIMAT0027622 |
| mir-1976 | GCAGCAAGGAAGGCAGGGGUCCUAAGGUGUGUCCUCC UGCCCUCCUUGCUGU (SEQ ID NO: 6); CCUCCUGCCCUCCUUGCUGU (SEQ ID NO: 7) | MI0009986; MIMAT0009451 |
| mir-550b-1 | AGAGACUUGUUGGAGAUGUGCCUGAGGGAGUAAGAC ACUAUCUUACAACAACAGGGCUCUUACUCCCUCAGGC ACUGCACCAGCCAGCAAAGCAUCA (SEQ ID NO: 8) | MI0016686 |
| mir-550b-2 | AGAGACUCGCUGGAGAUGUGCCUGAGGGAGUAAGACA CUAUCUGACAACAACAGGGCUCUUACUCCCUCAGGCA CUGCACCAGCCAGCAAAGCAUCA (SEQ ID NO: 9) | MI0016687 |
| miR-8071 | CGGUGGACUGGAGUGGGUGG (SEQ ID NO: 10); CGGCCACAUGGCCCAGGCUCUUCUCCGAGUGAUCUCG GUGGACUGGAGUGGGUGGUAGGUGGCAG (SEQ ID NO: 11) | MIMAT0030998; MI0025907; MI0026417 |
| miR-4481 | GGAGUGGGCUGGUGGUU (SEQ ID NO: 12); GGAGUGGGCUGGUGGUUUUUUAAGAGGAAGGGAGAC CUAAGCUAGCACAUGAGCACGCUC (SEQ ID NO: 13) | MIMAT0019015; MI0016842 |
| miR-3689b | GAUCCUGUGCUCCCUGGGGGGUCUGAUCCUGUGCUUC CUGGGAGGUGUGAUAUCAUGGUUCCUGGGAGGUGUG AUCCCGUGCUUCCUGGGAGGUGUGAUAUUGUGGUUCC UGGGAGGUGUGAUCCCGUGCUCCCUGGGAGGUGUGAU C (SEQ ID NO: 14); UGUGAUAUCAUGGUUCCUGGGA (SEQ ID NO: 15); CUGGGAGGUGUGAUAUUGUGGU (SEQ ID NO: 16) | MI0016411; MIMAT0018180; MIMAT0018181 |
| miR-629-3p | GUUCUCCCAACGUAAGCCCAGC (SEQ ID NO: 17) | MIMAT0003298 |
| miR-330-3p | GCAAAGCACACGGCCUGCAGAGA (SEQ ID NO: 18); GCAAAGCACAGGGCCUGCAGAGA (SEQ ID NO: 19) | MIMAT0000751; MIMAT0000569 |
| miR-501-3p | AAUGCACCCGGGCAAGGAUUCU (SEQ ID NO: 20); AAUGCACCCGGGCAAGGAUUUG (SEQ ID NO: 21) | MIMAT0004774; MIMAT0003509 |
| miR-7-1-3p | CAACAAAUCACAGUCUGCCAUA (SEQ ID NO: 22) | MIMAT0004553 |
| miR-128-3p | UCACAGUGAACCGGUCUCUUU (SEQ ID NO: 23) | MIMAT0000424 |
| miR-26b-5p | UUCAAGUAAUUCAGGAUAGGU (SEQ ID NO: 24) | MIMAT0000083; MIMAT0000534 |
| miR-125b-5p | UCCCUGAGACCCUAACUUGUGA (SEQ ID NO: 25) | MIMAT0000423 |
| miR-99a-5p | AACCCGUAGAUCCGAUCUUGUG (SEQ ID NO: 26) | MIMAT0000097 |
| miR-363-3p | AAUUGCACGGUAUCCAUCUGUA (SEQ ID NO: 27) | MIMAT0000707 |

As disclosed herein, a miRNA nucleic acid includes precursor miRNAs, as well processed or mature miRNA nucleic acids. For example, a miRNA nucleic acid may be a pri-miRNA, a pre-miRNA, or a mature miRNA nucleic acid. One of skill in the art can identify miRNA precursors, as well as processed or mature miRNAs.

In some examples, the miRNA nucleic acid of use in the methods disclosed herein has a sequence at least 90%, identical to the nucleic acid sequence of one of the miRNAs listed in Table 1. For example, the miRNA nucleic acid can have a nucleic acid sequence at least 90%, 91%, 92%, 93%, 94%, 95%, 96%, 97%, 98% or 99% identical to the nucleic acid sequence of one of the miRNAs listed in Table 1. Exemplary sequences can be obtained using computer programs that are readily available on the internet and the nucleic acid sequences set forth herein. In one example, the miRNA nucleic acid retains a function of the miRNA, such as hybridization to a miRNA target sequence.

In additional examples, a miRNA nucleic acid includes a miRNA nucleic acid that is slightly longer or shorter than the nucleotide sequence of any one of the miRNAs listed in Table 1, as long as the miRNA nucleic acid retains a function of the particular miRNA, such as hybridization to a miRNA target sequence. For example, a miRNA nucleic acid can include a few nucleotide deletions or additions at the 5'- or 3'-end of the nucleotide sequence of a miRNA listed in Table 1, such as addition or deletion of 1, 2, 3, 4, or more nucleotides from the 5'- or 3'-end, or combinations thereof (such as a deletion from one end and an addition to the other end). In particular examples, a mature miRNA nucleic acid is about 17 to 25 nucleotides in length (for example, 17, 18, 19, 20, 21, 22, 23, 24, or 25 nucleotides in length).

In other examples, a miRNA nucleic acid includes a miRNA mimic. In particular examples, a miRNA mimic is a RNA that mimics one or more of the miRNAs listed in Table 1 (for example, miR-25-3p, miR-629-3p, miR-330-3p, miR-501-3p, miR-7-1-3p, miR-128-3p, miR-26b-5p, miR-125b-5p, miR-99a-5p, miR-363-3p, mir-326, miR-6860, mir-6860, mir-1976, mir-550b-1, mir-550b-2, miR-8071, miR-4481, and mir-3689b). One of skill in the art can design and produce a miRNA mimic for a desired miRNA. miRNA mimics are also commercially available, for example MISSION® miRNA mimics from Sigma-Aldrich (St. Louis, Mo.) or miRIDIAN miRNA mimics (Thermo Scientific/Dharmacon RNAi Technologies, Lafayette, Colo.).

In some embodiments, the disclosed methods include a miRNA inhibitor or an miRNA inhibitor mimic. A miRNA inhibitor includes or consists of a nucleic acid molecule that is at least about 90% complementary to a miRNA nucleic acid, such as the nucleic acid sequence of a miRNA listed in Table 1. In some examples, a miRNA inhibitor includes or consists of a nucleic acid molecule that is at least about 90%, 91%, 92%, 93%, 94%, 95%, 96%, 97%, 98%, 99% or 100% complementary to nucleic acid sequence of a miRNA listed in Table 1. In particular examples, a miRNA inhibitor is about 17 to 25 nucleotides in length (for example, 17, 18, 19, 20, 21, 22, 23, 24, or 25 nucleotides in length). One of skill in the art can design and produce a miRNA inhibitor for a desired miRNA. miRNA inhibitors are also commercially available, for example Anti-miR™ miRNA inhibitors (Ambion, Austin, Tex.), miRIDIAN microRNA hairpin inhibitors (Thermo Scientific/Dharmacon, Lafayette, Colo.), or miScript miRNA inhibitors (Qiagen, Carlsbad, Calif.).

In one particular, non-limiting example, the miRNA is at least one of an miR-363-3p, miR-7-1-3p, miR-26b-5p, miR-125b-5p, or miR-128-3p nucleic acid. The at least one of an miR-363-3p, miR-7-1-3p, miR-26b-5p, miR-125b-5p, or miR-128-3p nucleic acid includes mature and precursor miRNA molecules, such as pri-RNA and pre-miRNA.

In particular examples, miR-363-3p, miR-7-1-3p, miR-26b-5p, miR-125b-5p, or miR-128-3p is at least one of a human miR-363-3p, miR-7-1-3p, miR-26b-5p, miR-125b-5p, or miR-128-3p. One of skill in the art can identify miR-363-3p, miR-7-1-3p, miR-26b-5p, miR-125b-5p, and miR-128-3p nucleic acids of use in the disclosed methods. For example, miR-363-3p, miR-7-1-3p, miR-26b-5p, miR-125b-5p, and miR-128-3p nucleic acids include miR-363-3p, miR-7-1-3p, miR-26b-5p, miR-125b-5p, or miR-128-3p sequences provided in miRBase (mirbase.org), such as miRBase Accession Nos. MIMAT0000707 and MIMAT0000708 (miR-363-3p); MIMAT0004553 (miR-7-1-3p); MIMAT0000083 and MIMAT0000534 (miR-26b-5p); MIMAT0000423 and MIMAT0000136 (miR-125b-5p); and MIMAT0000424 and MIMAT0000140 (miR-128-3p), all of which are incorporated herein by reference, as present in miRBase at least as of Oct. 27, 2016.

In other examples, an miR-363-3p, miR-7-1-3p, miR-26b-5p, miR-125b-5p, or miR-128-3p nucleic acid includes the sequences provided in GenBank, such as GenBank Accession Nos. NR_029852.1 (miR-363), NR_029605.1 (miR-7-1), NR_029500.1 (miR-26b), NR_029694.1 (miR-125b), and NR_029672.1 (miR-128), all of which are incorporated herein by reference, as present in GenBank at least as of Oct. 27, 2016.

Figure 2:
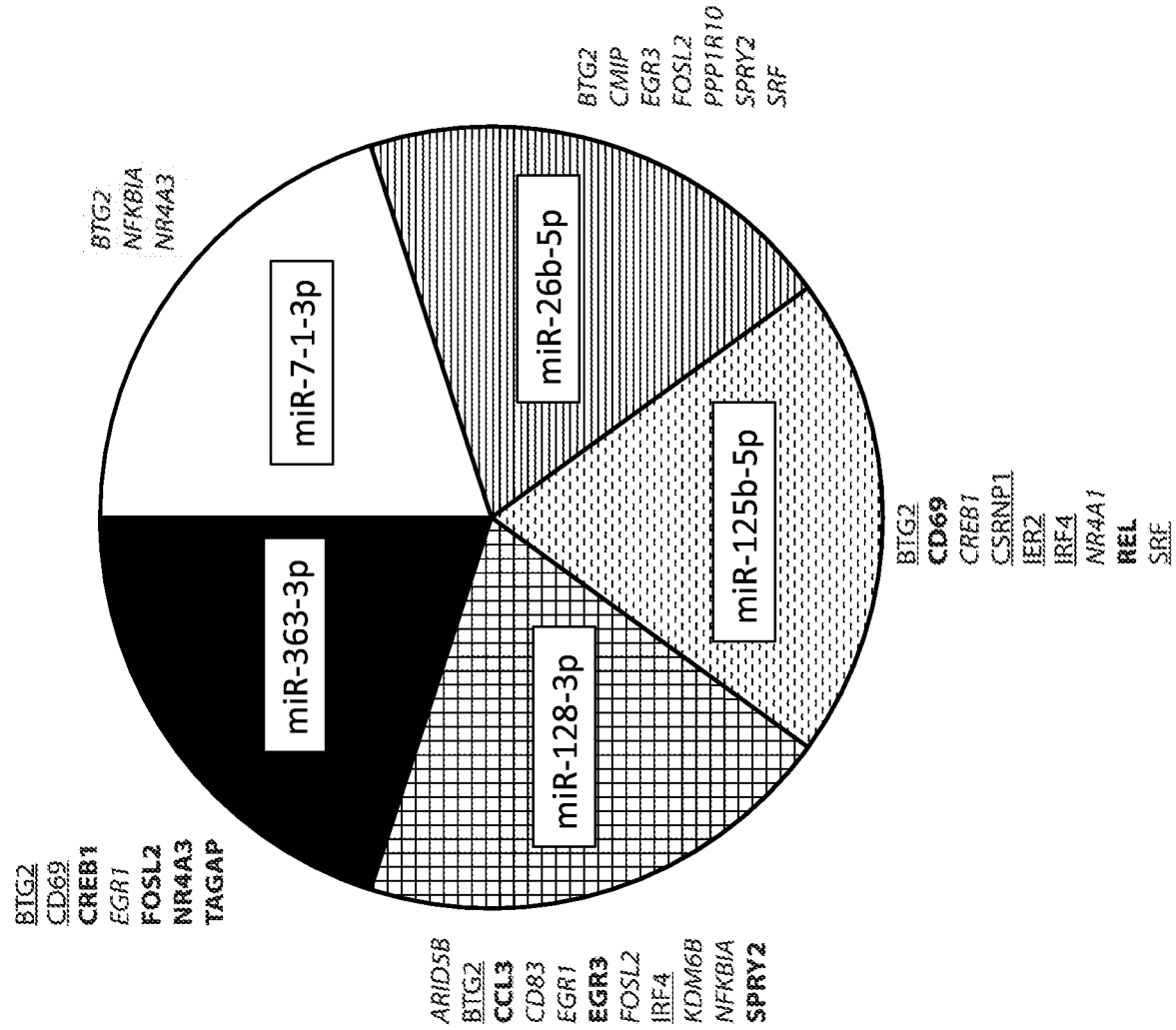
FIG. 2 shows target genes that are induced during T-cell activation in 1×g for five of the miRNAs that are downregulated during T-cell activation at 1×g but that are not regulated during T-cell activation in microgravity.
Figure 4:
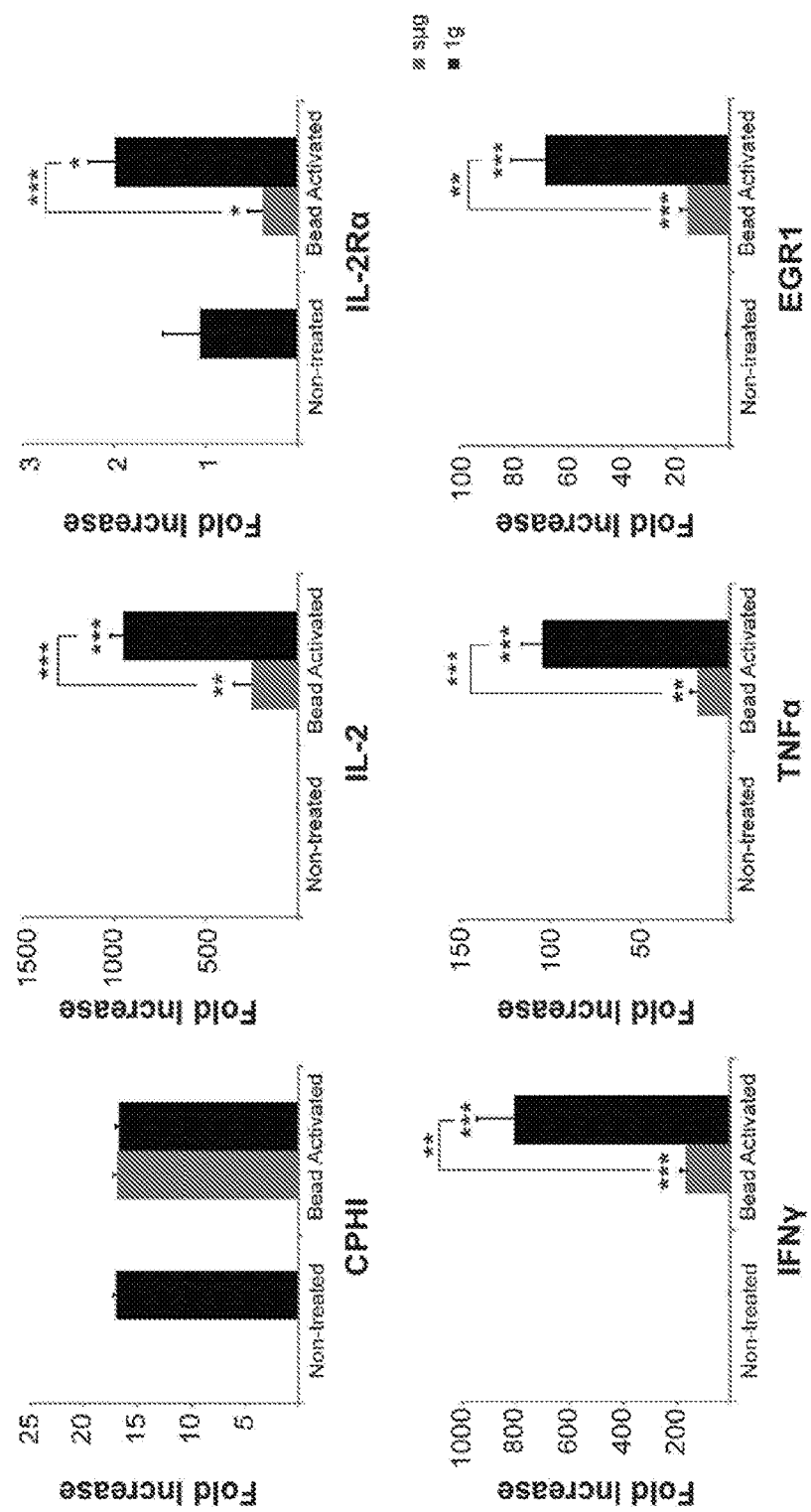
FIG. 4 are a series of graphs showing immune genes regulated by gravity in mice. Note that in microgravity, T cell activation is suppressed in both mice and humans.

In some examples, an miR-363-3p, miR-7-1-3p, miR-26b-5p, miR-125b-5p, or miR-128-3p nucleic acid specifically binds to a target gene or sequence and regulates gene expression (such as increasing or decreasing RNA or protein expression). In some examples, an miR-363-3p, miR-7-1-3p, miR-26b-5p, miR-125b-5p, or miR-128-3p nucleic acid target may include one or more of the RNAs shown in FIGS. 2 and 3.

Evaluating Expression in a Subject with or at Risk of an Immune System Condition Provided herein are methods for diagnosing an immune system condition in a subject (such as a human subject) and methods of treating a subject with an immune system condition. The immune system condition can be any type of immune system condition, such as primary diseases of the immune system (e.g., an inflammatory or autoimmune disorder) or can be immune system conditions that are associated with another condition and/or disease (e.g., human immunodeficiency virus infection or exposure to microgravity). The results of the disclosed assays offer a substantial clinical benefit because they can be used to distinguish subjects that have or are likely to have an immune system condition versus those that do not have or are not likely to have an immune system condition. Thus, the disclosed assays allow subjects to be accurately diagnosed and, if a subject has an immune system condition, to be accurately treated.

In additional examples, the methods are utilized to determine whether or not to provide the subject with therapeutic intervention. In one example, a therapeutic intervention is administered. Thus, if the subject has an immune system condition, a therapeutic intervention, such as miRNA therapy, other immunomodulatory therapy, non-steroidal anti-inflammatory drugs (NSAIDs), acetaminophen, corticosteroids, anti-inflammatory supplements, biologics, disease-modifying antirheumatic drugs (DMARDs), antimalarial drugs, stem cell or blood transfusion, physical therapy, and/or surgery, can be utilized. In particular examples, the therapeutic intervention is miRNA therapy. In specific examples, the miRNA therapy can include administering miRNA (such as human miRNA) or a mimic thereof or an inhibitor of miRNA or mimic thereof, or administering T cells contacted with miRNA or an inhibitor of miRNA (or mimics thereof). Any type of miRNA can be used, including pri-miRNA, a pre-miRNA, or a mature miRNA. Using the results of the disclosed assays to help distinguish subjects that have or are likely to have an immune system condition versus those that do not have or are not likely to have an immune system condition offers a substantial clinical benefit because, where the subject has an immune system condition, the methods disclosed herein allow the subject to be selected for therapeutic intervention.

Further provided are methods of diagnosing a subject with or at risk of an immune system condition and methods of treating a subject with an immune system condition, such as an immune system disorder (e.g., an inflammatory disorder, such as rheumatoid arthritis, chronic obstructive pulmonary lung disease, inflammatory bowel disease, or systemic lupus erythematosus, or an autoimmune disorder, such as multiple sclerosis, ankylosing spondylitis, celiac disease, Crohn's disease, Graves' disease, Hashimoto thyroiditis, or autoimmune uveitis) or can be immune system conditions that are associated with another condition and/or disease (e.g., human immunodeficiency virus infection or exposure to microgravity). Such methods can include measuring or detecting absolute or relative amounts of T cell activation-related markers present in a sample, such as a biological sample, tissue sample, and/or biological fluid sample obtained from a subject (e.g., a blood sample, for example plasma, whole blood, serum, and/or dried blood spots), for example using miRNA (e.g., mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p). In some examples, the T cell activation-related markers can include at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 or of (such as 1, 2, 3, 4, 5, 6, 7, 8, 9, 10, 11, 12, 13, 14, 15, 16, 17, 18, or 19 of) mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p. The expression levels of these markers can be measured. In some examples, the expression level measured can be compared to a control. Differential expression compared with a control includes differential levels of expression of one or more T cell activation-related marker of the subject compared to a control, such as at least 10% (such as 10%, 20%, 30%, 40%, 50%, 60%, 70%, 80%, 90%, 100%, or more) differential expression as compared to the control. If differential expression of the T cell activation-related markers (e.g., mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p) is measured in the sample, the methods can include administering therapeutic intervention to the subject, thereby treating the subject.

In some examples, measuring differential expression of the T cell activation-related markers can include measuring an increase in expression of the T cell activation-related markers relative to a control. In some examples, a control includes one or more of activated T cells, non-activated T cells, non-responsive T cells (such as from an elderly subject), or a subject or population of subjects without an immune system condition. For example, measuring an increase in expression of the T cell activation-related markers can include measuring an increase in expression of mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p. The expression of the T cell activation-related markers can be compared to an amount of the expression for each marker expected in a subject without an immune system condition, such as the median amount of expression in subjects without an immune system condition. For example, measuring differential expression of the T cell activation-related markers can include measuring increased expression of mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p relative to the amount of mir-326, miR-6860, mir-6860, mir-1976, mir-550b-1, mir-550b-2, miR-8071, miR-4481, mir-3689, miR-25-3p, miR-629-3p, miR-330-3p, miR-501-3p, miR-7-1-3p, miR-128-3p, miR-26b-5p, miR-125b-5p, miR-99a-5p, and/or miR-363-3p expression expected in a subject without an immune system condition. An increase in expression includes an increase in expression of one or more T cell activation-related marker (e.g., mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p) compared to a control, such as an increase in expression of at least 10% (such as 10%, 20%, 30%, 40%, 50%, 60%, 70%, 80%, 90%, 100%, or more) as compared to the control.

In other examples, measuring differential expression of the T cell activation-related markers can include measuring a decrease in expression of the T cell activation-related markers relative to a control. In some examples, a control includes one or more of activated T cells, non-activated T cells, non-responsive T cells (such as from an elderly subject), or a subject or population of subjects without an immune system condition. For example, measuring a decrease in expression of the T cell activation-related markers can include measuring a decrease in expression of mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p. The expression of the T cell activation-related markers can be compared to an amount of the expression for each marker expected in a subject without an immune system condition, such as the median amount of expression in subjects without an immune system condition. In other examples, measuring decreased expression of the T cell activation-related markers can include measuring decreased expression of mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p relative to the amount of mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p expression expected in a subject without an immune system condition.

A decrease in expression includes a decrease in expression of one or more T cell activation-related marker (e.g., mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p) compared to a control, such as a decrease in expression of at least 10% (such as 10%, 20%, 30%, 40%, 50%, 60%, 70%, 80%, 90%, 100%, or more) as compared to the control.

In some examples, measuring the expression of the T cell activation-related markers can include measuring more than one T cell activation-related marker, such as 1, 2, 3, 4, 5, 6, 7, 8, 9, 10, 11, 12, 13, 14, 15, 16, 17, 18, or 19 of) mir-326, miR-6860, mir-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p. In other examples, any combination of these markers can be measured. In particular examples, the combination of markers can include at least 1, at least 2, at least 3, at least 4, or all 5 of miR-7-1-3p, miR-128-3p, miR-26b-5p, miR-125b-5p, and/or miR-363-3p (such as 1, 2, 3, 4, or all 5 of miR-7-1-3p, miR-128-3p, miR-26b-5p, miR-125b-5p, and/or miR-363-3p).

In additional examples, measuring the expression of the T cell activation-related markers can include measuring the expression using a microarray analysis, a polymerase chain reaction (PCR) analysis, mass spectrometry analysis, and/or an immunohistochemistry analysis. In particular examples, measuring the expression of the T cell activation-related markers can include measuring the expression of miRNA (such as human miRNA) using a microarray analysis. The miRNA can be pri-miRNA, a pre-miRNA, or a mature miRNA. In certain examples, measuring the expression using a microarray analysis includes labeling at least one T cell activation-related miRNA using a detectable label. In specific examples, the detectable label is at least one of a fluorescent label, biotin, a radiolabel, an enzyme, and/or a calorimetric label. In certain specific examples, the detectable label is a fluorescent label.

Evaluating Nucleic Acid Expression

In some examples, expression of nucleic acids (e.g., miRNA) of T cell activation-related markers, such as the markers mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p, are analyzed and, in some examples, quantified. Suitable biological samples can include urine, blood, plasma, or serum samples obtained from a subject having or a subject at risk for immune system disorder (such as an inflammatory or autoimmune disorder). Differences in the amount of nucleic acid molecules for the T cell activation-related markers, such as mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p, in the sample indicates that the subject has an immune system disorder (e.g., an inflammatory disease or autoimmune disorder), as described herein. In some examples, the assay is multiplexed, in that expression of several nucleic acids are detected simultaneously or contemporaneously.

RNA can be isolated from a sample from a subject having or a subject at risk for an immune system disorder, such as a urine, blood, plasma, or serum sample, using methods well-known to one skilled in the art, including commercially available kits. General methods for mRNA extraction are well-known in the art and are disclosed in standard textbooks of molecular biology, including Ausubel et al., Current Protocols of Molecular Biology, John Wiley and Sons (1997). In one example, RNA isolation can be performed using a purification kit, buffer set, and protease from commercial manufacturers, such as QIAGEN®, according to the manufacturer's instructions. For example, total RNA from cells in culture (such as those obtained from a subject) can be isolated using QIAGIN® RNeasy mini-columns. Other commercially available RNA isolation kits include MASTERPURE® Complete DNA and RNA Purification Kit (EPICENTRE® Madison, Wis.) and Paraffin Block RNA Isolation Kit (Ambion, Inc.). Total RNA from tissue samples can be isolated using RNA Stat-60 (Tel-Test). RNA prepared from a biological sample can be isolated, for example, by cesium chloride density gradient centrifugation.

Methods of gene expression profiling include methods based on hybridization analysis of polynucleotides, methods based on sequencing of polynucleotides, and other methods in the art. In some examples, miRNA expression in a sample is quantified using northern blotting or in situ hybridization (Parker & Barnes, Methods in Molecular Biology 106:247-283, 1999); RNAse protection assays (Hod, *Biotechniques* 13:852-4, 1992); and PCR-based methods, such as reverse transcription polymerase chain reaction (RT-PCR) (Weis et al., *Trends in Genetics* 8:263-4, 1992). Alternatively, antibodies can be employed that can recognize specific duplexes, including DNA duplexes, RNA duplexes, and DNA-RNA hybrid duplexes or DNA-protein duplexes. Representative methods for sequencing-based gene expression analysis include Serial Analysis of Gene Expression (SAGE) and gene expression analysis by massively parallel signature sequencing (MPSS).

Methods for quantitating miRNA are well-known in the art. In one example, the method utilizes RT-PCR. For example, extracted RNA can be reverse-transcribed and the derived cDNA used as a template in the subsequent PCR reaction. A variation of RT-PCR that can be used is real time quantitative RT-PCR (qRT-PCR), which measures PCR product accumulation through a dual-labeled fluorogenic probe (e.g., TAQMAN® probe).

Although the PCR step can use a variety of thermostable DNA-dependent DNA polymerases, it typically employs the Taq DNA polymerase. TaqMan® PCR typically utilizes the 5'-nuclease activity of Taq or Tth polymerase to hydrolyze a hybridization probe bound to its target amplicon, but any enzyme with equivalent 5' nuclease activity can be used. Two oligonucleotide primers are used to generate an amplicon typical of a PCR reaction. A third oligonucleotide, or probe, is designed to detect nucleotide sequence located between the two PCR primers. The probe is non-extendible by Taq DNA polymerase enzyme and is labeled with a reporter fluorescent dye and a quencher fluorescent dye. Any laser-induced emission from the reporter dye is quenched by the quenching dye when the two dyes are located close together as they are on the probe. During the amplification reaction, the Taq DNA polymerase enzyme cleaves the probe in a template-dependent manner. The resultant probe fragments disassociate in solution, and the signal from the released reporter dye is free from the quenching effect of the second fluorophore. One molecule of reporter dye is liberated for each new molecule synthesized, and detection of the unquenched reporter dye provides the basis for quantitative interpretation of the data.

In some examples, miRNA expression is identified or confirmed using the microarray technique. In this method, nucleic acid sequences (e.g., probes) of interest (such as miRNA, cDNAs, and oligonucleotides) are plated or arrayed on a microchip substrate. The arrayed sequences are then hybridized with nucleic acids from a specific biological sample of interest. In a specific embodiment of the microarray technique, PCR-amplified inserts of cDNA clones are applied to a substrate in a dense array. Probes for the nucleotide sequences of T cell activation-related markers, such as mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p, are applied to the substrate, and the array can consist essentially of or consist of these sequences or of certain combinations of sequences for these markers. The microarrayed nucleic acids are suitable for hybridization under stringent conditions. Any type of label may be used for detection of the microarrayed nucleic acids, such as a fluorescent label, biotin, a radiolabel, an enzyme, a luminescent label, and/or a colorimetric label. Fluorescently labeled cDNA may be generated through incorporation of fluorescent nucleotides by reverse transcription of RNA extracted from tissues or samples of interest. Labeled cDNA applied to the chip hybridize with specificity to each spot of DNA on the array. After stringent washing to remove non-specifically bound probes, the chip is analyzed. Quantitation of hybridization of each arrayed element allows for assessment of corresponding mRNA abundance. With dual color fluorescence, separately labeled cDNA generated from two sources of RNA are hybridized pairwise to the array. The relative abundance of the transcripts from the two sources corresponding to each specified gene is thus determined simultaneously. Such methods have the sensitivity required to detect rare transcripts, which are expressed at a few copies per cell, and to reproducibly detect at least approximately two-fold differences in the expression levels (Schena et al., *Proc. Natl. Acad. Sci. USA* 93(2):10614-9, 1996). Microarray analysis can be performed by commercially available equipment, following manufacturer's protocols, such as are supplied with Affymetrix GenChip technology or Incyte's microarray technology.

Serial analysis of gene expression (SAGE) is another method that allows the simultaneous and quantitative analysis of a large number of gene transcripts without the need for providing an individual hybridization probe for each transcript. First, a short sequence tag (about 10-14 base pairs) is generated that contains sufficient information to uniquely identify a transcript, provided that the tag is obtained from a unique position within each transcript. Then, many transcripts are linked together to form long serial molecules that can be sequenced, revealing the identity of the multiple tags simultaneously. The expression pattern of any population of transcripts can be quantitatively evaluated by determining the abundance of individual tags and identifying the gene corresponding to each tag. For more details see, for example, Velculescu et al., *Science* 270:484-7, 1995, and Velculescu et al., *Cell* 88:243-51, 1997.

In further examples, miRNA expression is identified or confirmed using the mass spectrometry (MS) technique. Various MS applications for measuring miRNA are known in the art (e.g., Kullolli et al., J Am Soc Mass Spectrom, 25(1): 80-87, 2014; Kim et al., PLoS One, 11(7): e0153201, 2016, both of which are incorporated herein by reference). An electrospray ionization- or matrix-assisted laser-desorption ionization (MALDI)-based method may be used. Tandem mass spectrometry (MS/MS) applications may also be used. Multiplex applications are also possible, which facilitates analysis of multiple miRNA simultaneously.

Methods of Treating an Immune System Condition and/or Altering T Cell Activation Provided herein are methods for treating an immune system condition and/or altering T cell activation in a subject (such as a human subject). In some examples, the methods include administering to the subject miRNA (or an miRNA mimic) and/or an inhibitor of miRNA (or an inhibitor of miRNA mimic), thereby treating the immune system condition and/or altering the T cell activation. Methods of inhibiting and expressing miRNA are known, such as the methods of Christopher et al., Perspect Clin Res., 7(2): 68-74, 2016, and Baumann and Winkler, Future Med Chem., 6(17): 1967-1984, 2014, both of which are incorporated herein by reference. Any type of miRNA (e.g., human miRNA or a mimic thereof) can be administered, such as pri-miRNA, pre-miRNA, and/or mature miRNA. In particular examples, an miRNA inhibitor or mimic thereof can be administered. In some non-limiting examples, the miRNA inhibitor can be a nucleic acid at least 80%, at least 85%, at least 90%, at least 95%, at least 96%, at least 97%, at least 98%, at least 99%, or 100% complementary to a mature miRNA, or about 90% identical to a mature miRNA. In other examples, the methods include administering to the subject T cells contacted with miRNA (or an miRNA mimic) and/or an inhibitor of miRNA. The T cells can be contacted with the miRNA and/or an inhibitor of miRNA in vivo or in vitro. In some non-limiting examples, the T cells can be activated before the T cells are contacted with miRNA and/or an inhibitor of miRNA.

In some examples, the methods include administering to a subject of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 of (such as 1, 2, 3, 4, 5, 6, 7, 8, 9, 10, 11, 12, 13, 14, 15, 16, 17, 18, or 19 of) of mir-326, mir-6860, miR-6860, mir-1976, mir-550b-1, mir-550b-2, miR-8071, miR-4481, and/or mir-3689b and/or an inhibitor of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof. In specific examples, the methods include administering to a subject of at least 1, at least 2, at least 3, at least 4, or all 5 of (such as 1, 2, 3, 4, or 5 of) an inhibitor of miR-7-1-3p, miR-128-3p, miR-26b-5p, miR-125b-5p, and/or miR-363-3p, or a mimic thereof. In other examples, the methods include administering at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 of (such as 1, 2, 3, 4, 5, 6, 7, 8, 9, 10, 11, 12, 13, 14, 15, 16, 17, 18, or 19 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p or a mimic thereof and/or an inhibitor of mir-326, mir-6860, miR-6860, mir-1976, mir-550b-1, mir-550b-2, miR-8071, miR-4481 and/or mir-3689b, or a mimic thereof. In particular examples, the methods include administering to a subject of at least 1, at least 2, at least 3, at least 4, or all 5 of (such as 1, 2, 3, 4, or 5 of) of miR-7-1-3p, miR-128-3p, miR-26b-5p, miR-125b-5p, and/or miR-363-3p or a mimic thereof.

In other examples, the methods include administering to the subject T cells contacted with miRNA and/or an inhibitor of miRNA or a mimic thereof. In some examples, the methods include contacting T cells with of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 of (such as 1, 2, 3, 4, 5, 6, 7, 8, 9, 10, 11, 12, 13, 14, 15, 16, 17, 18, or 19 of) of mir-326, mir-6860, miR-6860, mir-1976, mir-550b-1, mir-550b-2, miR-8071, miR-4481, and/or mir-3689b and/or an inhibitor of miR-25-3p, miR-629-3p, miR-330-3p, miR-501-3p, miR-7-1-3p, miR-128-3p, miR-26b-5p, miR-125b-5p, miR-99a-5p, and/or miR-363-3p or a mimic thereof. In specific examples, the methods include contacting T cells with at least 1, at least 2, at least 3, at least 4, or all 5 of (such as 1, 2, 3, 4, or 5 of) an inhibitor of miR-7-1-3p, miR-128-3p, miR-26b-5p, miR-125b-5p, and/or miR-363-3p or a mimic thereof. In other examples, the methods include contacting T cells with at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 of (such as 1, 2, 3, 4, 5, 6, 7, 8, 9, 10, 11, 12, 13, 14, 15, 16, 17, 18, or 19 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p and/or an inhibitor of mir-326, mir-6860, miR-6860, mir-1976, mir-550b-1, mir-550b-2, miR-8071, miR-4481 and/or mir-3689b or a mimic thereof. In particular examples, the methods include contacting the T cells with at least 1, at least 2, at least 3, at least 4, or all 5 of (such as 1, 2, 3, 4, or 5 of) miR-7-1-3p, miR-128-3p, miR-26b-5p, miR-125b-5p, and/or miR-363-3p or a mimic thereof.

In some examples, the methods include activating T cells before the T cells are contacted with miRNA and/or an inhibitor of miRNA. In specific non-limiting examples, the activating T cells includes increasing T cell proliferation and/or increasing T cell cytokine (e.g., interleukin (IL)-2, IL-4, IL-6, IL-17, tumor necrosis factor (TNF)-α, interferon (IFN)-γ, and/or granulocyte-macrophage colony-stimulating factor) production, and/or T cell chemokine (e.g., CCL3 and/or XCL2) production. In other non-limiting examples, the T cell can be a CD4+ T cell and/or a CD8+ T cell. In still further examples, the T cells can be activated by contacting the T cells with CD28 and/or concanavalin A.

The methods can include selecting a subject in need of altered T cell activation. In some non-limiting examples, the methods include selecting a subject that does not have activated T cells (such as a subject with an immunodeficiency or immunosuppression). Where the subject does not have activated T cells, the methods can include administering to the subject an effective amount of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or at least 19 of mir-326, mir-6860, miR-6860, mir-1976, mir-550b-1, mir-550b-2, miR-8071, miR-4481, and/or mir-3689b or a mimic thereof, and/or an inhibitor of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby increasing T cell activation. In specific examples, where the subject does not have activated T cells, the methods include administering to the subject a therapeutically effective amount of at least 1, at least 2, at least 3, at least 4, or all 5 of (such as 1, 2, 3, 4, or 5 of) of an inhibitor of miR-7-1-3p, miR-128-3p, miR-26b-5p, miR-125b-5p, and/or miR-363-3p, or a mimic thereof, thereby increasing T cell activation. In other examples, where the subject has activated T cells (such as a subject with cytokine storm and/or an inflammatory and/or autoimmune disease), the methods can include administering to the subject an effective amount of at least 1, at least 2, at least 4, at least 5, at least 6, at least 7, at least 8, at least 9, at least 10, at least 11, at least 12, at least 13, at least 14, at least 15, at least 16, at least 17, at least 18, or all 19 or of (such as 1, 2, 3, 4, 5, 6, 7, 8, 9, 10, 11, 12, 13, 14, 15, 16, 17, 18, or 19 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p or a mimic thereof and/or an inhibitor of mir-326, mir-6860, miR-6860, mir-1976, mir-550b-1, mir-550b-2, miR-8071, miR-4481 and/or mir-3689b, or a mimic thereof, thereby decreasing T cell activation. In particular examples, where the subject has activated T cells, the methods include administering to the subject a therapeutically effective amount of at least 1, at least 2, at least 3, at least 4, or all 5 of (such as 1, 2, 3, 4, or 5 of) of miR-7-1-3p, miR-128-3p, miR-26b-5p, miR-125b-5p, and/or miR-363-3p, thereby decreasing T cell activation.

In other non-limiting examples, the methods include administering to a subject T cells with altered (e.g., increased or decreased) activation. The methods can include contacting T cells with miRNA and/or an inhibitor of miRNA, thereby altering T cell activation. In some examples, the T cells are contacted with an effective amount of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 or of (such as 1, 2, 3, 4, 5, 6, 7, 8, 9, 10, 11, 12, 13, 14, 15, 16, 17, 18, or 19 of) of mir-326, mir-6860, mir-1976, mir-550b-1, mir-550b-2, miR-8071, miR-4481, and/or mir-3689, or a mimic thereof, and/or an inhibitor of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby increasing T cell activation. In specific examples, the T cells are contacted with an effective amount of at least 1, at least 2, at least 3, at least 4, or all 5 of (such as 1, 2, 3, 4, or 5 of) of an inhibitor of miR-7-1-3p, miR-128-3p, miR-26b-5p, miR-125b-5p, and/or miR-363-3p, or a mimic thereof, thereby increasing T cell activation. In other examples, the T cells are contacted with an effective amount of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 or of (such as 1, 2, 3, 4, 5, 6, 7, 8, 9, 10, 11, 12, 13, 14, 15, 16, 17, 18, or 19 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof and/or an inhibitor of mir-326, mir-6860, miR-6860, mir-1976, mir-550b-1, mir-550b-2, miR-8071, miR-4481 and/or mir-3689b, or a mimic thereof, thereby decreasing T cell activation. In particular examples, the T cells are contacted with an effective amount of at least 1, at least 2, at least 3, at least 4, or all 5 of (such as 1, 2, 3, 4, or 5 of) of miR-7-1-3p, miR-128-3p, miR-26b-5p, miR-125b-5p, and/or miR-363-3p, or a mimic thereof, thereby decreasing T cell activation. The methods can further include activating the T cells before contacting the T cells with one or more miRNAs and/or inhibitors of miRNA.

In some examples, the methods include selecting a subject with an immune system condition. The immune system condition can be any type of immune system condition, such as a cytokine storm, an immune system disorder (e.g., an inflammatory or autoimmune disorder) or can be immune system conditions associated with another condition and/or disease (e.g., human immunodeficiency virus infection or exposure to microgravity). In some non-limiting examples, the immune system condition is an inflammatory disorder. In specific embodiments, the inflammatory disorder can be rheumatoid arthritis, chronic obstructive pulmonary lung disease, inflammatory bowel disease, or systemic lupus erythematosus. In other examples, the immune system condition is an autoimmune disorder. In certain embodiments, the autoimmune disorder is type I diabetes, multiple sclerosis, lupus erythematosus, myasthenia gravis, ankylosing spondylitis, celiac disease, Crohn's disease, Graves' disease, Hashimoto's thyroiditis, or autoimmune uveitis. In still further examples, the immune system condition is exposure or anticipated exposure to microgravity. In particular embodiments, the microgravity exposure is due to the subject's presence aboard a space shuttle, the International Space Station, a satellite, or a rocket while in flight outside the Earth's atmosphere. In other embodiments, the microgravity exposure is simulated microgravity, for example, due to Earth-based conditions that mimic microgravity, such as balancing gravity with equal and opposite forces, including shear force, centripetal force, Coriolis forces, buoyancy, and/or a magnetic field.

The immune system condition can include an underactive or an overactive immune response. In some non-limiting examples, immune system condition includes an underactive immune response. In particular examples, the immune system condition that includes an underactive immune response is primary immunodeficiency (such as a genetic or non-hereditary immunodeficiency) or immunodeficiency associated with another disease or condition (such as immunosuppression due to human immunodeficiency virus infection, exposure to microgravity, leukemia, chemotherapy and radiation, poor nutrition or malnutrition, and/or excessive injuries that predispose the subject to infections). Where the immune system condition includes an underactive immune response, the methods can include administering to the subject a therapeutically effective amount of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 of (such as 1, 2, 3, 4, 5, 6, 7, 8, 9, 10, 11, 12, 13, 14, 15, 16, 17, 18, or 19 of) mir-326, mir-6860, miR-6860, mir-1976, mir-550b-1, mir-550b-2, miR-8071, miR-4481, and/or mir-3689b and/or an inhibitor of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby treating the immune system condition. In specific examples, where the immune system condition includes an underactive immune response, the methods can include administering to the subject a therapeutically effective amount of at least 1, at least 2, at least 3, at least 4, or all 5 of (such as 1, 2, 3, 4, or 5 of) an inhibitor of miR-7-1-3p, miR-128-3p, miR-26b-5p, miR-125b-5p, and/or miR-363-3p, or a mimic thereof, thereby treating the immune system condition.

In other non-limiting examples, the immune system condition includes an overactive immune response. In particular examples, the immune system condition that includes an overactive immune response is cytokine storm, an inflammatory disorder (such as rheumatoid arthritis, chronic obstructive pulmonary lung disease, inflammatory bowel disease, or systemic lupus erythematosus) or an autoimmune disorder (such as type I diabetes, multiple sclerosis, lupus erythematosus, myasthenia gravis, ankylosing spondylitis, celiac disease, Crohn's disease, Graves' disease, Hashimoto's thyroiditis, or autoimmune uveitis). Where the immune system condition includes an overactive immune response, the methods can include administering to the subject a therapeutically effective amount of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 of (such as 1, 2, 3, 4, 5, 6, 7, 8, 9, 10, 11, 12, 13, 14, 15, 16, 17, 18, or 19 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p and/or an inhibitor of mir-326, mir-6860, miR-6860, mir-1976, mir-550b-1, mir-550b-2, miR-8071, miR-4481 and/or mir-3689b, or a mimic thereof, thereby treating the immune system condition. In particular examples, where the immune system condition includes an overactive immune response, the methods can include administering to the subject a therapeutically effective amount of at least 1, at least 2, at least 3, at least 4, or all 5 of (such as 1, 2, 3, 4, or 5 of) miR-7-1-3p, miR-128-3p, miR-26b-5p, miR-125b-5p, and/or miR-363-3p, or a mimic thereof.

In other non-limiting examples, the methods include administering to a subject a therapeutically effective amount of T cells with altered activation, thereby treating the immune system condition. In some examples, the immune system condition includes an underactive immune response, and the methods include contacting the T cells with an effective amount of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 or of (such as 1, 2, 3, 4, 5, 6, 7, 8, 9, 10, 11, 12, 13, 14, 15, 16, 17, 18, or 19 of) mir-326, mir-6860, miR-6860, mir-1976, mir-550b-1, mir-550b-2, miR-8071, miR-4481, and/or mir-3689b, or a mimic thereof and/or an inhibitor of miR-25-3p, miR-629-3p, miR-330-3p, miR-501-3p, miR-7-1-3p, miR-128-3p, miR-26b-5p, miR-125b-5p, miR-99a-5p, and/or miR-363-3p, or a mimic thereof, thereby increasing T cell activation. In specific examples, the immune system condition includes an underactive immune response, and the methods include contacting the T cells with an effective amount of at least 1, at least 2, at least 3, at least 4, or all 5 of (such as 1, 2, 3, 4, or 5 of) an inhibitor of miR-7-1-3p, miR-128-3p, miR-26b-5p, miR-125b-5p, and/or miR-363-3p or a mimic thereof. In other examples, where the immune system condition includes an overactive immune response, the methods can include contacting T cells with an effective amount of at least 1, at least 2, at least 3, at least 4, at least 5, at least 6, at least 7, at least 8, at least 9, at least 10, at least 11, at least 12, at least 13, at least 14, at least 15, at least 16, at least 17, at least 18, or all 19 of (such as 1, 2, 3, 4, 5, 6, 7, 8, 9, 10, 11, 12, 13, 14, 15, 16, 17, 18, or 19 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p and/or an inhibitor of mir-326, mir-6860, miR-6860, mir-1976, mir-550b-1, mir-550b-2, miR-8071, miR-4481 and/or mir-3689b, or a mimic thereof, thereby decreasing T cell activation. In particular examples, where the immune system condition includes an overactive immune response, the methods can include contacting T cells with an effective amount of at least 1, at least 2, at least 3, at least 4, or all 5 of (such as 1, 2, 3, 4, or 5 of) miR-7-1-3p, miR-128-3p, miR-26b-5p, miR-125b-5p, and/or miR-363-3p or a mimic thereof. The methods can further include activating the T cells before contacting the T cells with miRNA and/or an inhibitor of miRNA.

Compositions Useful in Methods of Treating an Immune System Condition and/or Altering T Cell Activation Provided herein are compositions for treating immune system conditions and/or altering T cell activation, including compositions with one or more pharmaceutically acceptable carriers, such as pharmaceutically acceptable carriers that provide for both local (such as topical or inhalational) and/or systemic (such as oral or intravenous) use to treat the various immune system conditions described herein. Therefore, the disclosure includes within its scope pharmaceutical compositions formulated for use in human or veterinary medicine that include the compositions for treating immune system conditions. A suitable administration format may best be determined by a medical practitioner for each subject individually. Various pharmaceutically acceptable carriers and their formulation are described in standard formulation treatises, e.g., *Remington's Pharmaceutical Sciences* by E. W. Martin. See also Wang, Y. J. and Hanson, M. A., *Journal of Parenteral Science and Technology*, Technical Report No. 10, Supp. 42: 2S, 1988. The dosage form of the pharmaceutical composition will be determined by the mode of administration chosen.

Subjects in need of altered T cell activation, subjects with an immune system condition, and/or subjects analyzed with the disclosed methods and who are found to have an immune system condition, for example, subjects found to have altered expression (such as increased and/or decreased expression) of T cell activation-related miRNA, such as mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p, can be selected for treatment. In some examples, subjects with or at risk for an immune system condition found to have increased expression of T cell activation-related miRNA, such as mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p can be administered therapy for the immune system condition. In some examples, subjects with or at risk for an immune system condition found to have decreased expression of T cell activation-related miRNA, such as mir-326, mir-6860, miR-6860, mir-1976, mir-550b-1, mir-550b-2, miR-8071, miR-4481, mir-3689b, miR-25-3p, miR-629-3p, miR-330-3p, miR-501-3p, miR-7-1-3p, miR-128-3p, miR-26b-5p, miR-125b-5p, miR-99a-5p, and/or miR-363-3p, can be administered therapy for the immune system condition. In some examples, subjects analyzed with the disclosed methods and who are found to have differential expression (such as increased and/or decreased expression) of T cell activation-related miRNA may be treated using at least one of miRNA therapy, other immunomodulatory therapy, non-steroidal anti-inflammatory drugs (NSAIDs), acetaminophen, corticosteroids, anti-inflammatory supplements, biologics, disease-modifying antirheumatic drugs (DMARDs), antimalarial drugs, blood transfusion, physical therapy, and/or surgery, thereby treating the subject.

In some examples, subjects in need of altered T cell activation (such as increased T cell activation), subjects with an immune system condition (such as an immunodeficiency and/or immunosuppression), and/or subjects analyzed with the disclosed methods and who are found to have increased expression of at least 1, at least 2, at least 3, at least 4, at least 5, at least 6, at least 7, or all 8 of (such as 1, 2, 3, 4, 5, 6, 7, or 8 of) mir-326, mir-6860, miR-6860, mir-1976, mir-550b-1, mir-550b-2, miR-8071, miR-4481 and/or mir-3689b and/or decreased expression of at least 1, at least 2, at least 3, at least 4, at least 5, at least 6, at least 7, at least 8, at least 9, of all 10 of (such as 1, 2, 3, 4, 5, 6, 7, 8, 9, or 10 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p (for example, decreased expression of at least 1, at least 2, at least 3, at least 4, or all 5 of miR-7-1-3p, miR-128-3p, miR-26b-5p, miR-125b-5p, and/or miR-363-3p, such as 1, 2, 3, 4, or all 5 of miR-7-1-3p, miR-128-3p, miR-26b-5p, miR-125b-5p, and/or miR-363-3p) may be treated using miRNA therapy, other immunomodulatory therapy (including biologics and anti-infection drugs, such as including antibodies, immunoglobulin therapy, and/or vaccine therapy), and/or medical procedures (including stem cell transplant).

In some examples, subjects in need of altered T cell activation (such as decreased T cell activation), subjects with an immune system condition (such as cytokine storm and/or an inflammatory and/or autoimmune disorder), and/or subjects analyzed with the disclosed methods and who are found to have decreased expression of at least 1, at least 2, at least 3, at least 4, at least 5, at least 6, at least 7, or all 8 of (such as 1, 2, 3, 4, 5, 6, 7, or 8 of) mir-326, mir-6860, miR-6860, mir-1976, mir-550b-1, mir-550b-2, miR-8071, miR-4481 and/or mir-3689b and/or increased expression of at least 1, at least 2, at least 3, at least 4, at least 5, at least 6, at least 7, at least 8, at least 9, of all 10 of (such as 1, 2, 3, 4, 5, 6, 7, 8, 9, or 10 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p (for example, increased expression of at least 1, at least 2, at least 3, at least 4, or all 5 of miR-7-1-3p, miR-128-3p, miR-26b-5p, miR-125b-5p, and/or miR-363-3p, such as 1, 2, 3, 4, or all 5 of miR-7-1-3p, miR-128-3p, miR-26b-5p, miR-125b-5p, and/or miR-363-3p) may be treated using miRNA therapy, other immunomodulatory therapy (including biologics), anti-inflammatory drugs and/or supplements, disease-modifying antirheumatic drugs (DMARDs), antimalarial drugs, and/or medical procedures.

In some examples, subjects in need of altered T cell activation, subjects with an immune system condition, and/or subjects analyzed with the disclosed methods and who are found to have altered expression (such as increased and/or decreased expression) of T cell activation-related miRNA may be treated using miRNA therapy. The methods can include administering miRNA therapeutically by inhibiting and/or expressing certain microRNA (see, e.g., Christopher et al., Perspect Clin Res., 7(2): 68-74, 2016, and Baumann and Winkler, Future Med Chem., 6(17): 1967-1984, 2014, both of which are incorporated herein by reference). In specific examples, administering miRNA therapy can include administering miRNA (such as human miRNA or miRNA mimics) or an inhibitor of miRNA (such as human miRNA inhibitor or miRNA inhibitor mimics) or administering T cells contacted with miRNA or an inhibitor of miRNA or mimics thereof. The methods can include inhibition of microRNA by microRNA antagonists (e.g., antisense nucleotides) and microRNA replacement, such as with microRNA and/or microRNA mimics. Any type of miRNA can be used, including pri-miRNA, a pre-miRNA, or a mature miRNA. The miRNA therapy can be administered locally, such as to a cell, tissue, and/or organ, or it can be administered systemically. The miRNA or miRNA inhibitor may be included in a composition including one or more pharmaceutically acceptable carriers and/or adjuvants, including such carriers as liposomes, exosomes, peptides, and nanoparticles. One of skill in the art can determine dosages and route of administration, for example, based on the potency of the specific formulation and the age, weight, sex, and physiological condition of the subject.

In specific, non-limiting embodiments, the miRNA therapy includes contacting T cells with the miRNA (or an miRNA mimic) and/or an miRNA inhibitor (or an miRNA inhibitor mimic), such as contacting the T cells with the miRNA and/or miRNA inhibitor in vitro, and then administering the T cells to the subject. The T cells may be introduced to a subject in need of increased T cell activation and/or a subject with an immune condition, such as immunodeficiency (e.g., in an immunocompromised subject, an elderly subject, a subject with cancer, or a subject which is exposed to or will be exposed to microgravity). In other embodiments, the T cells may be introduced to a subject in need of decreased T cell activation and/or a subject with an immune condition, such as an autoimmune or inflammatory disorder. In some examples, the T cells are autologous to the subject. A sample (such as a blood sample) including T cells is obtained from the subject. In some examples, T cells are isolated from the sample. In other examples, the T cells are already activated. In still further examples, where the T cells (either isolated T cells or T cells present in the sample from the subject) are not activated T cells, the T cells can be incubated with agents to activate the T cells (such as an antigen presenting cell with an MHC molecule bound to an antigen, anti-CD28 and ConA, or anti-CD3 antibodies (if the subject is human)) for a sufficient amount of time to activate the T cells in the sample, such as at least 10 minutes (for example, at least 15 minutes, 20 minutes, 30 minutes, 40 minutes, 1 hour, 1.5 hours, 2 hours, 3 hours, or more).

In some examples, the T cells are activated for about 2-24 hours.

The activated T cells in the sample are contacted with a miRNA inhibitor or mimic thereof (such as an inhibitor of one or more of miR-25-3p, miR-629-3p, miR-330-3p, miR-501-3p, miR-7-1-3p, miR-128-3p, miR-26b-5p, miR-125b-5p, miR-99a-5p, or miR-363-3p, for example, an inhibitor of one or more of miR-363-3p, such as 1, 2, 3, 4, or all 5 of miR-7-1-3p, miR-128-3p, miR-26b-5p, miR-125b-5p, or miR-363-3p) or a miRNA (such as one or more of mir-326, mir-6860, miR-6860, mir-1976, mir-550b-1, mir-550b-2, miR-8071, miR-4481, or mir-3689b) that increases activation of the T cells. In other embodiments, the activated T cells in the sample are contacted with miRNA or miRNA mimic (such as one or more of miR-25-3p, miR-629-3p, miR-330-3p, miR-501-3p, miR-7-1-3p, miR-128-3p, miR-26b-5p, miR-125b-5p, miR-99a-5p, or miR-363-3p, for example, one or more of miR-363-3p, such as 1, 2, 3, 4, or all 5 of miR-7-1-3p, miR-128-3p, miR-26b-5p, miR-125b-5p, or miR-363-3p) or an miRNA inhibitor (such as an inhibitor of one or more of mir-326, mir-6860, miR-6860, mir-1976, mir-550b-1, mir-550b-2, miR-8071, miR-4481, or mir-3689b) that decreases activation of the T cells. The activated T cells are contacted with the miRNA or miRNA inhibitor or mimic thereof for at least 10 minutes (for example, at least 15 minutes, 20 minutes, 30 minutes, 40 minutes, 1 hour, 1.5 hours, 2 hours, 3 hours, 4 hours, 8 hours, 12 hours, 18 hours, 24 hours, 36 hours, 48 hours, 72 hours, or more). In some examples, the activated T cells are contacted with one or more miRNAs, miRNA mimics, or miRNA inhibitors or mimics for about 1-48 hours).

In some examples, the resulting T cells with increased activation are then introduced into a subject in need of increased T cell activation and/or a subject with an immune condition, such as immunodeficiency (e.g., in an immunocompromised and/or immunosuppressed subject, an elderly subject, a subject with cancer, or a subject which is exposed to or will be exposed to microgravity). In other examples, the resulting T cells with decreased activation are then introduced into a subject in need of decreased T cell activation and/or a subject with an immune condition, such as an autoimmune or inflammatory disorder. In other examples, the resulting T cells with increased or decreased activation are then re-introduced into the same subject from which they originated. The T cells with increased or decreased activation treat or inhibit at least one symptom of the subject. For example, the T cells with increased activation treat or inhibit at least one symptom of a decreased immune response, such as in a subject with an immunodeficiency, or the T cells with decreased activation treat or inhibit at least one symptom of an overactive immune response, such as in a subject with an inflammatory and/or autoimmune disorder.

Other therapies of use for the methods disclosed herein can be administered alone or in combination with miRNA therapy. Exemplary therapies include other immunomodulatory therapies, anti-inflammatory drugs and/or supplements, disease-modifying antirheumatic drugs (DMARDs) and/or antimalarial drugs, and/or medical procedures (including surgery and stem cell transplantation).

In some examples, subjects analyzed with the disclosed methods and who are found to have altered expression (such as increased and/or decreased expression) of T cell activation-related miRNA may be treated using other immunomodulatory therapies, including biologics. In certain examples, subjects analyzed with the disclosed methods and who are found to have increased expression of at least 1, at least 2, at least 3, at least 4, at least 5, at least 6, at least 7, or all 8 of (such as 1, 2, 3, 4, 5, 6, 7, or 8 of) mir-326, mir-6860, miR-6860, mir-1976, mir-550b-1, mir-550b-2, miR-8071, miR-4481 and/or mir-3689b and/or decreased expression of at least 1, at least 2, at least 3, at least 4, at least 5, at least 6, at least 7, at least 8, at least 9, of all 10 of (such as 1, 2, 3, 4, 5, 6, 7, 8, 9, or 10 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p (for example, decreased expression of at least 1, at least 2, at least 3, at least 4, or all 5 of miR-7-1-3p, miR-128-3p, miR-26b-5p, miR-125b-5p, and/or miR-363-3p, such as 1, 2, 3, 4, or all 5 of miR-7-1-3p, miR-128-3p, miR-26b-5p, miR-125b-5p, and/or miR-363-3p) may be treated by administering agents that block pathways that inhibit T cell activation (e.g., using anti-cytotoxic T lymphocyte antigen (CTLA)-4 antibodies and anti-programmed cell death (PD)-1 antibodies alone or in combination with each other and/or other with other treatments), by administering modulatory cytokines (e.g., IL-2 and IL-7), by administering agents that modulate mechanistic target of rapamycin (mTOR; e.g., by administering rapamycin to enhance CD8 T cell immunity), using antimicrobial therapy (e.g., vaccination, antifungals, and/or antibiotics), using T cell adoptive transfer (i.e., transfusion of in vitro cultivated T cells; in some examples, the T cells are engineered for an enhanced immune response, such by contacting the T cells with miRNA, e.g., using miRNA therapy, using biologics that target immunomodulatory pathways (e.g., muromonab, ipilimumab, abatacept, belatacept, tremelimumab, BMS-936558, CT-011, MK-3475, AMP224, BMS-936559, MPDL3280A, MEDI4736, MGA271, IMP321, BMS-663513, PF-05082566, CDX-1127, anti-OX40, huMAb, OX40L, and TRX518; Yao et al., Nat Rev Drug Discov, 12(2): 130-146, 2013; Kamphorst et al., Vaccine, 33(0 2): B21-B28, 2015, both of which are incorporated herein by reference).

In other examples, subjects analyzed with the disclosed methods and who are found to have decreased expression of at least 1, at least 2, at least 3, at least 4, at least 5, at least 6, at least 7, or all 8 of (such as 1, 2, 3, 4, 5, 6, 7, or 8 of) mir-326, mir-6860, miR-6860, mir-1976, mir-550b-1, mir-550b-2, miR-8071, miR-4481 and/or mir-3689b and/or increased expression of at least 1, at least 2, at least 3, at least 4, at least 5, at least 6, at least 7, at least 8, at least 9, of all 10 of (such as 1, 2, 3, 4, 5, 6, 7, 8, 9, or 10 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p (for example, increased expression of at least 1, at least 2, at least 3, at least 4, or all 5 of miR-7-1-3p, miR-128-3p, miR-26b-5p, miR-125b-5p, and/or miR-363-3p, such as 1, 2, 3, 4, or all 5 of miR-7-1-3p, miR-128-3p, miR-26b-5p, miR-125b-5p, and/or miR-363-3p) may be treated using immunosuppressive agents (e.g., for preventing rejection of transplanted organs or tissues, treating autoimmune diseases, and/or inflammatory diseases; e.g., glucocorticoids, such as prednisone, dexamethasone, and hydrocortisone; cytostatics, such as alkylating agents and antimetabolites; antibodies, such as Atgam, thymoglobuline, and T-cell receptor- and IL-2 receptor-directed antibodies; immunophilin-targeting agents, such as cyclosporin, tacrolimus, sirolimus, and everolimus; interferons (IFNs), such as IFNλ and IFNβ; opioids; TNF binding proteins, such as infliximab, etanercept, and adalimumab; mycophenolate; and small biological agents, such as fingolimod and myriocin), immune tolerance therapy (e.g., for treating subjects at risk for tissue or organ transplantation rejection, subjects with allergies, and/or subjects with autoimmune disease; e.g., T or B cell-targeting or T or B cell-suppressing drugs, such as CAMPATH-1H, calcineurin inhibitors, rituximab, epratuzumab, belimumab, and atacicept; anti-cluster of differentiation (CD)3 antibodies; abatacept; induction of hematopoietic chimerism, such as mixed hematopoietic chimerism, in which the bone marrow of an organ or a tissue recipient is replaced with the donor's bone marrow or a mixture of the donor and recipient bone marrow to reduce organ or tissue transplant rejection; antigen desensitization; see Nepom et al., Immunol Rev; 241(1): 49-62, 2011, incorporated herein by reference), antihistamines, helminthic therapies (e.g., deliberate infestation of the subject with a helminth or with the ova of a helminth for treating immune disorders).

In some examples, subjects analyzed with the disclosed methods and who are found to have altered expression (such as increased and/or decreased expression) of T cell activation-related miRNA may be treated using anti-inflammatory drugs and/or supplements. In particular examples, subjects analyzed with the disclosed methods and who are found to have decreased expression of at least 1, at least 2, at least 3, at least 4, at least 5, at least 6, at least 7, or all 8 of (such as 1, 2, 3, 4, 5, 6, 7, or 8 of) mir-326, mir-6860, miR-6860, mir-1976, mir-550b-1, mir-550b-2, miR-8071, miR-4481 and/or mir-3689b and/or increased expression of at least 1, at least 2, at least 3, at least 4, at least 5, at least 6, at least 7, at least 8, at least 9, of all 10 of (such as 1, 2, 3, 4, 5, 6, 7, 8, 9, or 10 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p (for example, increased expression of at least 1, at least 2, at least 3, at least 4, or all 5 of miR-7-1-3p, miR-128-3p, miR-26b-5p, miR-125b-5p, and/or miR-363-3p, such as 1, 2, 3, 4, or all 5 of miR-7-1-3p, miR-128-3p, miR-26b-5p, miR-125b-5p, and/or miR-363-3p) may be treated using nonsteroidal anti-inflammatory drugs, such as NSAIDS (e.g., agents that inhibit the cyclooxygenase enzyme; e.g., aspirin, ibuprofen, and naproxen), antileukotrines, immune selective anti-inflammatory derivatives (ImSAIDs); bioactive compounds with anti-inflammatory activities (e.g., plumbagin and plumericin); steroids (e.g.,); applying ice to inflamed tissue; and/or anti-inflammatory supplements (e.g., bromelain, cannabinoids, honokiol, Nigella sative, hyperforin, coal tar, and omega-3 fatty acids).

In some examples, subjects analyzed with the disclosed methods and who are found to have altered expression (such as increased and/or decreased expression) of T cell activation-related miRNA may be treated using disease-modifying antirheumatic drugs (DMARDs) and/or antimalarial drugs. In specific examples, subjects analyzed with the disclosed methods and who are found to have decreased expression of at least 1, at least 2, at least 3, at least 4, at least 5, at least 6, at least 7, or all 8 of (such as 1, 2, 3, 4, 5, 6, 7, or 8 of) mir-326, mir-6860, miR-6860, mir-1976, mir-550b-1, mir-550b-2, miR-8071, miR-4481 and/or mir-3689b and/or increased expression of at least 1, at least 2, at least 3, at least 4, at least 5, at least 6, at least 7, at least 8, at least 9, of all 10 of (such as 1, 2, 3, 4, 5, 6, 7, 8, 9, or 10 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p (for example, increased expression of at least 1, at least 2, at least 3, at least 4, or all 5 of miR-7-1-3p, miR-128-3p, miR-26b-5p, miR-125b-5p, and/or miR-363-3p, such as 1, 2, 3, 4, or all 5 of miR-7-1-3p, miR-128-3p, miR-26b-5p, miR-125b-5p, and/or miR-363-3p) may be treated using disease-modifying antirheumatic drugs (DMARDs) and/or antimalarial drugs.

Disease-modifying antirheumatic drugs (DMARDs) include drugs that are otherwise unrelated drugs but are defined by their use in rheumatoid arthritis to slow down disease progression and reduce evidence of the process underlying the disease. However, DMARDS can also be used to treat other inflammatory and autoimmune diseases (e.g., Crohn's disease, lupus erythematosus (SLE), Sjogren's Syndrome, immune thrombocytopenic purpura (ITP), myasthenia gravis, and sarcoidosis). DMARDS of use include small molecular weight drugs that are chemically synthesized, such as methotrexate, sulfasalazine, leflunomide, hydroxychloroquine, and tofacitinib, and/or biological agents produced through genetic engineering, such as tumor necrosis factor (TNF)-alpha inhibitors (e.g., infliximab, etanercept, adalimumab, certolizumab, and golimumab), interleukin inhibitors (e.g., tocilizumab and anakinra), T-cell activation inhibitors (e.g., abatacept), and CD-20 activity blockers (e.g., rituximab; see Atzinger and Guo, Am Health Drug Benefits, 10(1): 27-36, 2017, incorporated herein by reference). The dosage of DMARDS administered to a subject varies depending on several factors, including the efficacy and toxicity for a specific subject (Cohen et al., U.S. Patent Pub. No. 2004/0022787, providing examples of specific dosages; Guidelines for the Management of Rheumatoid Arthritis, Arthritis and Rheumatism Vol. 39, No. 5, May 1996, pages 713-711; Physician's Desk Reference 2002, Medical Economics Company, Inc. Montvale, N.J. 07645, all of which are incorporated herein by reference).

Antimalarial drugs are drugs that are designed to prevent or cure malaria; however, some antimalarial drugs, such as chloroquine and hydroxychloroquine, can also be used to treat other inflammatory and autoimmune disease (e.g., rheumatoid arthritis and lupus-associated arthritis). Antimalarial drugs of use for in the methods disclosed herein (e.g., for treating inflammatory and autoimmune diseases) are known in the art (see, e.g., U.S. Pat. No. 9,308,213 and Intl. Pub. No. 2006/108666, both of which are incorporated herein by reference). The dose of the drug depends on the type and variety of the disease. Examples of antimalarial drugs of use in the methods described herein can include amodiaquine, an artemisinin (e.g., arteether, artemether, artemisinin, artesunate, and dihydroartemisinin), atovaquone, chloroquine, clindamycin, doxycycline, halofantrine, hydroxychloroquine, mefloquine, primaquine, proguanil, pyrimethamine, quinacrine, quinines and related agents (e.g., quinimax and quinidine), rufigallol, and sulfonamides (e.g., sulfadoxine and sulfamethoxypyridazine; U.S. Pat. No. 9,308,213 and Intl. Pub. No. 2006/108666, describing exemplary antimalarial drugs and dosages, both of which are incorporated herein by reference).

In some examples, subjects analyzed with the disclosed methods and who are found to have altered expression (such as increased and/or decreased expression) of T cell activation-related miRNA may be treated using a medical procedure. In certain examples, subjects analyzed with the disclosed methods and who are found to have increased expression of at least 1, at least 2, at least 3, at least 4, at least 5, at least 6, at least 7, or all 8 of (such as 1, 2, 3, 4, 5, 6, 7, or 8 of) mir-326, mir-6860, miR-6860, mir-1976, mir-550b-1, mir-550b-2, miR-8071, miR-4481 and/or mir-3689b and/or decreased expression of at least 1, at least 2, at least 3, at least 4, at least 5, at least 6, at least 7, at least 8, at least 9, of all 10 of (such as 1, 2, 3, 4, 5, 6, 7, 8, 9, or 10 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p (for example, decreased expression of at least 1, at least 2, at least 3, at least 4, or all 5 of miR-7-1-3p, miR-128-3p, miR-26b-5p, miR-125b-5p, and/or miR-363-3p, such as 1, 2, 3, 4, or all 5 of miR-7-1-3p, miR-128-3p, miR-26b-5p, miR-125b-5p, and/or miR-363-3p) may be treated using stem cell and/or thymus tissue transplantation and/or surgery to treat related complications (e.g., endoscopic sinus surgery to treat chronic sinusitis, splenectomy to treat severe autoimmune thrombocytopenia or hemolytic anemia. In other examples, subjects analyzed with the disclosed methods and who are found to have decreased expression of at least 1, at least 2, at least 3, at least 4, at least 5, at least 6, at least 7, or all 8 of (such as 1, 2, 3, 4, 5, 6, 7, or 8 of) mir-326, mir-6860, miR-6860, mir-1976, mir-550b-1, mir-550b-2, miR-8071, miR-4481 and/or mir-3689b and/or increased expression of at least 1, at least 2, at least 3, at least 4, at least 5, at least 6, at least 7, at least 8, at least 9, of all 10 of (such as 1, 2, 3, 4, 5, 6, 7, 8, 9, or 10 of) miR-25-3p, miR-629-3p, miR-330-3p, miR-501-3p, miR-7-1-3p, miR-128-3p, miR-26b-5p, miR-125b-5p, miR-99a-5p, and/or miR-363-3p (for example, increased expression of at least 1, at least 2, at least 3, at least 4, or all 5 of miR-7-1-3p, miR-128-3p, miR-26b-5p, miR-125b-5p, and/or miR-363-3p, such as 1, 2, 3, 4, or all 5 of miR-7-1-3p, miR-128-3p, miR-26b-5p, miR-125b-5p, and/or miR-363-3p) may be treated using stem cell transplantation, physical therapy and/or acupuncture (e.g., to treat autoimmune disorders and/or relieve pain associated with inflammation), surgery to treat related complications (e.g., liver transplant to treat autoimmune hepatitis; synovectomy, tendon repair, joint fusion, and/or total joint replacement to treat rheumatoid arthritis; joint replacement to treat osteoarthritis; colectomy and/or proctocolectomy to treat ulcerative colitis or Crohn's disease; bowel resection and/or stricturoplasty to treat Crohn's disease; appendectomy to treat appendicitis), plasmapheresis (e.g., to treat autoimmune disorders), and/or nerve stimulation (e.g., to relieve pain associated with inflammation).

Therapeutic compositions can be provided as parenteral compositions, such as for injection or infusion. Such compositions are formulated generally by mixing a disclosed therapeutic agent at the desired degree of purity in a unit dosage injectable form (solution, suspension, or emulsion) with a pharmaceutically acceptable carrier, for example, one that is non-toxic to recipients at the dosages and concentrations employed and is compatible with other ingredients of the formulation. In addition, a disclosed therapeutic agent can be suspended in an aqueous carrier, for example, in an isotonic or hypotonic buffer solution at a pH of about 3.0 to about 8.5, such as about 4.0 to about 8.0, about 6.5 to about 8.5, or about 7.2. Useful buffers include saline-buffered phosphate or an ionic boric acid buffer. The active ingredient, optionally together with excipients, can also be in the form of a lyophilisate and can be made into a solution prior to parenteral administration by the addition of suitable solvents. Solutions such as those that are used, for example, for parenteral administration can also be used as infusion solutions.

Pharmaceutical compositions can include an effective amount of the polypeptide, nucleic acid molecule, or dispersed (for example, dissolved or suspended) in a pharmaceutically acceptable carrier or excipient. Pharmaceutically acceptable carriers and/or pharmaceutically acceptable excipients are known in the art and are described, for example, in Remington's Pharmaceutical Sciences by E. W. Martin, Mack Publishing Co., Easton, Pa., 19th Edition (1995).

The nature of the carrier will depend on the particular mode of administration being employed. For example, parenteral formulations usually contain injectable fluids that include pharmaceutically and physiologically acceptable fluids, such as water, physiological saline, balanced salt solutions, aqueous dextrose, glycerol, or the like, as a vehicle. For solid compositions (such as powder, pill, tablet, or capsule forms), conventional non-toxic solid carriers can include, for example, pharmaceutical grades of mannitol, lactose, starch, or magnesium stearate. In addition, pharmaceutical compositions to be administered can contain minor amounts of non-toxic auxiliary substances, such as wetting or emulsifying agents, preservatives, pH buffering agents and the like, for example, sodium acetate or sorbitan monolaurate.

As used herein, "pharmaceutically acceptable carrier" includes any and all solvents, dispersion media, coatings, antibacterial and antifungal agents, isotonic and absorption delaying agents, and the like. The use of such media and agents for pharmaceutically active substances is well-known in the art. Except insofar as any conventional media or agent is incompatible with the active ingredient, its use in the pharmaceutical compositions is contemplated. Supplementary active ingredients also can be incorporated into the compositions. For example, certain pharmaceutical compositions can include the vectors or viruses in water, mixed with a suitable surfactant, such as hydroxypropylcellulose. Dispersions also can be prepared in glycerol, liquid polyethylene glycols, and mixtures thereof as well as in oils. Under ordinary conditions of storage and use, these preparations contain a preservative to prevent the growth of microorganisms.

Administration of therapeutic compositions can be by any common route as long as the target tissue is available via that route. This includes oral, nasal, ocular, buccal, or other mucosal (such as rectal or vaginal) or topical administration. Alternatively, administration will be by orthotopic, intradermal subcutaneous, intramuscular, intraperitoneal, or intravenous injection routes. Such pharmaceutical compositions are usually administered as pharmaceutically acceptable compositions that include physiologically acceptable carriers, buffers, or other excipients. Pharmaceutical compositions can be formulated with an appropriate solid or liquid carrier, depending upon the particular mode of administration chosen.

The pharmaceutically acceptable carriers and excipients useful in this disclosure are conventional. For instance, parenteral formulations usually comprise fluids that are pharmaceutically and physiologically acceptable fluid vehicles, such as water, physiological saline, other balanced salt solutions, aqueous dextrose, glycerol, or the like. Excipients that can be included are, for instance, proteins, such as human serum albumin, or plasma preparations. If desired, the pharmaceutical composition to be administered may also contain minor amounts of non-toxic auxiliary substances, such as wetting or emulsifying agents, preservatives, pH buffering agents, and the like, for example, sodium acetate or sorbitan monolaurate.

The dosage form of the pharmaceutical composition will be determined by the mode of administration chosen. For instance, in addition to injectable fluids, topical and oral formulations can be employed. Oral formulations may be liquid (e.g., syrups, solutions, or suspensions) or solid (e.g., powders, pills, tablets, or capsules). For solid compositions, conventional non-toxic solid carriers can include pharmaceutical grades of mannitol, lactose, starch, or magnesium stearate. Actual methods of preparing such dosage forms are known or will be apparent to those of ordinary skill in the art. Implants can also be employed.

The pharmaceutical compositions will, in some embodiments, be formulated in unit dosage form, suitable for individual administration of precise dosages. The amount of active compound(s) administered will depend on the subject being treated, the severity of the affliction, and the manner of administration and is best left to the judgment of the prescribing clinician. Within these bounds, the formulation to be administered will contain a quantity of the active component(s) in amounts effective to achieve the desired effect in the subject being treated.

The disclosure is illustrated by the following non-limiting Examples.

EXAMPLES

Example 1 miRNA Regulation in Activated T Cells in Spaceflight

This example describes miRNA levels in activated T cells in a microgravity environment.

Methods & Materials

Human Blood Donors:

Ten LRS chambers from individual donors were obtained for each launch attempt. Complete blood counts were provided for each donor. Additionally, all donor blood was tested as directed by the Food and Drug Administration and American Association of Blood Banks and negative for hepatitis B, hepatitis C, HIV, HTLV, syphilis, and West Nile Virus. Aseptic laboratory techniques were used to maintain the sterility and quality of human donor samples. For simulated microgravity data, buffy coats met all of the qualifications described above. There were a total of 8 preparations due to launch scrubs.

CD4+ T-Cell Isolation:

Human donor blood was diluted with Hank's BSS without Ca+/Mg+. Peripheral blood mononuclear cells (PBMC) were isolated by FICOLL-PAQUE™ PLUS (GE™ Healthcare, Pittsburgh, Pa.) density centrifugation. Following two washes, the cells were resuspended in sterile filtered EASYSEP™ Buffer (dPBS with 2% FBS, 1 mM EDTA) according to manufacturer's protocol (STEMCELL™ Technologies, Vancouver, BC, Canada). CD4+ T-Cell Isolation was performed using EASYSEP™ Human CD4+ T Cell Negative selection Enrichment Kit and Easy 50 EASYSEP™ Magnet according to the manufacturer's protocol (STEMCELL™ Technologies, Vancouver, BC, Canada). For spaceflight samples, $8\times10^6$ cells were resuspended in 1 ml in RPMI 1640 media (THERMO FISHER', Waltham, Mass.) supplemented with 1% L-glutamine, antibiotics, glucose-pyruvate, 1.2% HEPES buffer, and 10% FBS. Rotating wall vessel (RWV)-simulated microgravity samples were resuspended at $20\times10^6$ cells in 10 ml supplemented RPMI media.

Spaceflight Hardware:

Kayser Italia (KI) provided spaceflight hardware, including 12 experimental units (EUs), 10 experimental containers (ECs), and proper experimental hardware (EH). Each EU housed 4 independent donors. A total of 10 EUs (n=8) were used with 5 different conditions: a) Non-Treated (NT) μg, b) 1.5 hr Activated (Act) μc) 1.5 hr Act 1 g, d) 4 hr Act μg, e) 4 hr Act 1 g. Each culture chamber (CC) was loaded with $8\times10^6$ human T cells. The activator piston was filled for a final concentration of 15 μg/ml concanavalin A (SIGMA-ALDRICH™, St. Louis, Mo.)+6 μg/ml anti-CD28 (BD™ Biosciences, San Diego, Calif.). A fixative reservoir was filled with RNAPROTECT™ Cell Reagent (QIAGEN™, Valencia, Calif.).

SpaceX CRS-5 (SpX-5) Operations:

Samples were placed aboard SpaceX CRS-5 (SpX-5), which launched from Cape Canaveral SLC-40, FL. The EC were installed into a pre-warmed KUBIK incubator three days after launch in static (μg) and centrifuge (1 g) positions. Samples were activated following a 2-h incubation at 37° C. and fixed at the time points described above. The fixed samples were stored at −20° C. until the flight returned. The temperature was monitored by three IBUTTON™ Temperature Data Loggers for the NT as well as 1.5 h and 4 h ECs. The CRS landed near the coast of Southern California one month after launch. Frozen samples were obtained on the following day. The samples were thawed and sterilely removed from the EUs for RNA extraction.

Leukin Spaceflight Operations:

The onboard operations and timeline for mRNA samples have been previously described (1). A refined analysis of that data for the gene list was performed (FIG. 3).

Simulated Microgravity:

For simulated microgravity experiments, T cells were loaded into 10 ml disposable rotating wall vessels (RWV) and used with a rotary cell culture system (ROTARY CELL CULTURE SYSTEMS™, Synthecon, Inc, Houston, Tex.) in a standard incubator (37° C., 5% CO2). RWVs contain an internal membrane allowing gas exchange and are rotated synchronously such that the time-averaged gravitational vector on the cells is a leg force that approximates microgravity. Following overnight pre-rotation, the cells were activated with final concentration of 15 μg/ml concanavalin A and 6 μg/ml anti-CD28 per vessel. Non-treated cells received an equal volume of RPMI media. At 1.5 h, the cells were pelleted, fixed with 600 µl of an RNA-stabilizing reagent (RNAPROTECT™) and stored at −80° C. until further analysis.

Microarray Sample Preparation and Analysis

RNA Isolation and Processing:

RNA isolation and processing for mRNA has been previously described (1). RNA for miRNA microarrays was isolated using an RNA isolation kit (RNEASY™ mini kit, QIAGEN™, Valencia, Calif.) according to the manufacturer's protocol. Samples were stored at −80° C. until further analysis. The quantity and purity of purified RNA was determined using a spectrometer (NANODROP™). RNA from spaceflight samples had initial 260 nm/280 nm values between 1.6 and 2.2. The total RNA (0.93 µg) at the 1.5 h time point was processed. A biotin-labeling kit was used (FlashTag Biotin HSR RNA Labeling Kit, AFFYMETRIX™, Santa Clara, Calif.). Labeled cDNA was hybridized to human microarrays (human GENECHIP™ miRNA v4.0 microarray, AFFYMETRIX™) based on Sanger release 20. The signal intensity fluorescent images produced during the microarray hybridizations (AFFYMETRIX™ GENECHIP™) were read using a microarray scanner (AFFYMETRIX™ model 3000 scanner) and converted into probe result files (GENECHIP™ probe result files; e.g., *.CEL files) using signal estimation and quality control functionality software (COMMAND CONSOLE™ and EXPRESSION CONSOLE™, AFFYMETRIX™).

Microarray Analysis:

Microarray data were analyzed using gene analysis and statistical software (GENESPRING™ GX 14.5 software, AGILENT TECHNOLOGIES™, Santa Clara, Calif., USA). miRNA data (n=3) were analyzed as previously described (1). miRNA data (n=4) were normalized using the RMA algorithm, and the baseline normalization was the average level of expression in µg non-activated T cells. Low-signal probes (20% or lower) were filtered to remove background noise. Nineteen human miRNAs the expression for which was up- or down-regulated between 1×g and µg by at least 1.2 fold were identified using a moderated T-test with Benjamini-Hochberg multiple testing correction and a p-value ≤0.05. An miRNA target gene clustering analysis was performed using gene analysis and statistical software (GENESPRING™ GX 14.5) with an Euclidian similarity measure with Ward's linkage.

RNA Isolation and Real-Time (RT) Quantitative PCR (qRT-PCR):

The RT reaction was performed using a High Capacity cDNA reverse Transcription Kit with an RNAse Inhibitor (APPLIED BIOSYSTEMS™, Foster City, Calif.). The total RNA (0.3 µg) was added to 30 µl RT reaction mix prepared per the manufacturer's protocol, except Oligo d(T)16 (APPLIED BIOSYSTEMS™) was used in place of the Random Primers in the kit. The reaction was incubated at 25° C. for 10 min, 37° C. for 2 h, inactivated at 85° C. for 5 min, and held at 4° C. The cDNA (2 µl) from the RT reaction was added to 20 µl qRT-PCR containing 10 µl X-SYBR Green PCR Master Mix (APPLIED BIOSYSTEMS™) and 12 pmol oligonucleotide primers. PCR experiments were performed using a real-time PCR detection system (BIO-RAD™ CFX96 TOUCH™ Real-Time PCR Detection System or BIO-RAD™ MYIQ' Single Color Real-Time PCR Detection System). The thermal profile was 95° C. for 10 min, followed by 40 amplification cycles consisting of denaturation at 95° C. for 15 seconds, annealing at 60° C. for 30 seconds, and elongation at 72° C. for 30 seconds. Fluorescence of the qRT-PCR reaction was measured using PCR analysis software (BIO-RAD™ CFX MANAGER™ software, BIO-RAD™ Laboratories, Hercules, Calif.) and used to quantify mRNA expression. Following amplification, a melt curve analysis confirmed the amplicon specificity.

RNA samples were normalized to cyclophilinA (Cphi) as an internal standard. The relative fold increase of gene expression was calculated by using the 2 ΔΔCt equation, where Ct represents the comparative threshold. Gene abundance calculations were performed using the equation 1/(2 Ct gene T−Ct CPHI T) as previously described (2). The resulting values were then multiplied by 1000 for better graphical presentation. Statistical analysis of abundance data was performed using repeated measures ANOVA with a post-hoc Tukey-Kramer test. Primers used were designed using primer analysis software (OLIGO™ Primer Analysis Software, Molecular Biology Insights, Cascade, Colo.) and were manufactured by Eurofins Genomics (Huntsville, Ala.). In some cases, the sequences for primers were developed directly from the Harvard Primer Bank (3).

Analysis

Figure 1B:
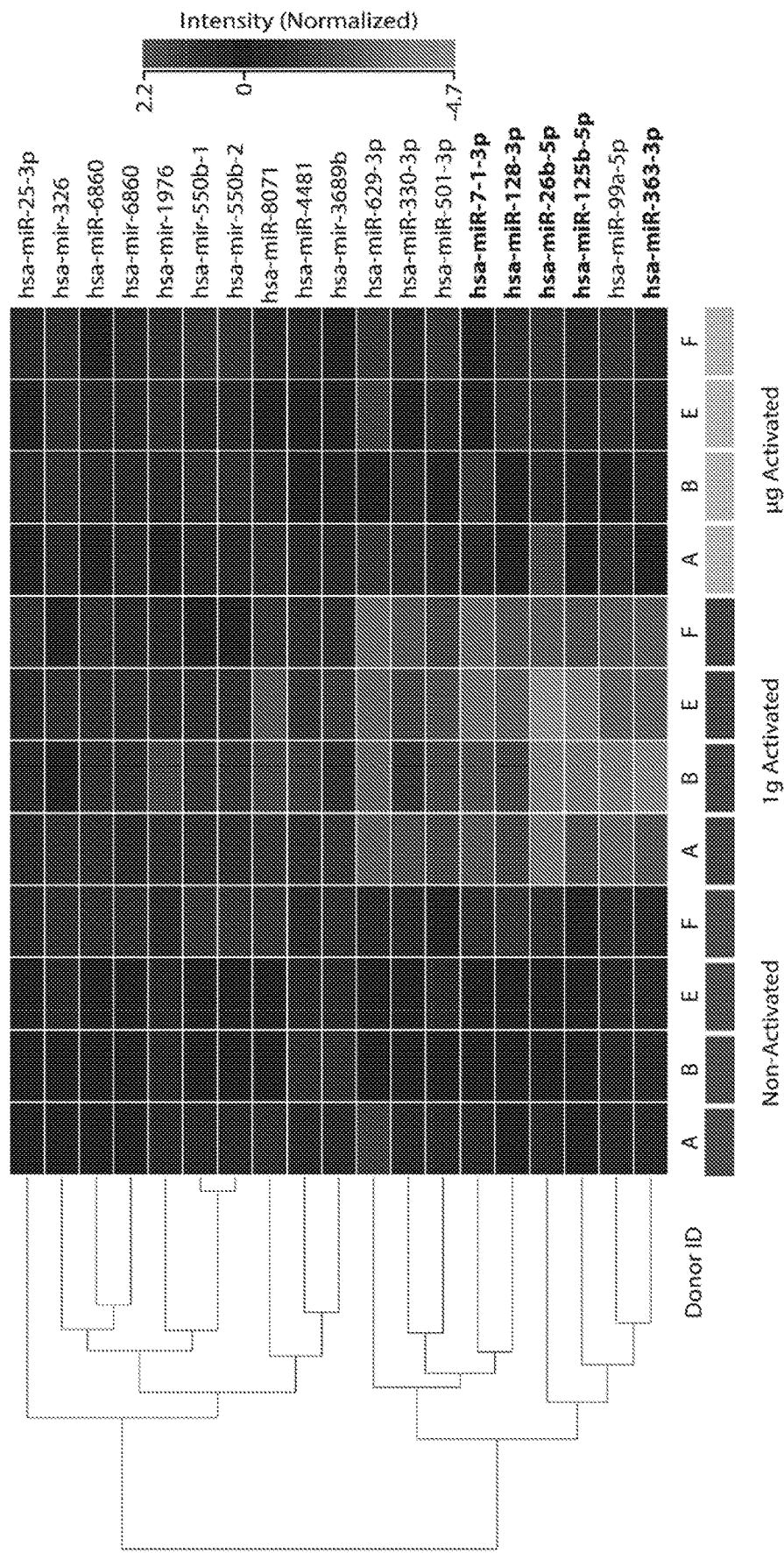
FIG. 1B is a heat map of downregulated or upregulated miRNAs during T-cell activation at 1 g that are not regulated during T-cell activation in microgravity within 1.5 hours as determined in a SpaceX5 experiment. Each column represents individual patients for each condition.

T cells from individual donors were launched to the International Space Station (ISS). Some cells were activated at 1×g as controls, while other cells were activated in microgravity. Non-activated controls were used. CD4+ T cells were activated with Concanavalin A (ConA) and anti-CD28 for 1.5 hours. The miRNA samples were loaded on Affymetrix gene arrays (U133) and analyzed using Gene-Spring software (Agilent Technologies, Santa Clara, Calif.). Heat maps showing changes in mRNA (FIG. 1A) and miRNA (FIG. 1B) expression were generated. A total of 19 miRNAs exhibiting sensitivity to gravity (significance of <0.05 and at least 1.5-fold change in expression) are shown in Table 2 and FIG. 1B. Of these 19 genes, 9 have identified target genes, and 5 have certain target genes that are induced during T-cell activation at 1 g (exemplified, but not limited) by the genes shown in FIG. 2).

TABLE 2

Significantly altered miRNAs during first hours of activation compared to untreated and microgravity samples. Identified mRNA targets for miRNA in bold (TargetScan7), and identified target genes that are induced during T-cell activation at 1 g for miRNA in bold with italics; µg, microgravity; NT, untreated control.

| miRNA ID | p-value (Benjamini-Hochberg MTC) | Fold Change 1 × g ConA vs µg ConA | Regulation 1 × g vs µg | Fold Change 1 × g ConA vs NT | Regulation 1 × g vs NT |
|---|---|---|---|---|---|
| hsa-miR-25-3p | 0.05 | −1.68 | down | −1.54 | down |
| hsa-mir-326 | 0.04 | 1.94 | up | 1.35 | up |
| hsa-miR-6860 | 0.05 | 1.70 | up | 1.78 | up |

TABLE 2-continued

Significantly altered miRNAs during first hours of activation compared to untreated and microgravity samples. Identified mRNA targets for miRNA in bold (TargetScan7), and identified target genes that are induced during T-cell activation at 1 g for miRNA in bold with italics; μg, microgravity; NT, untreated control.

| miRNA ID | p-value (Benjamini-Hochberg MTC) | Fold Change 1 × g ConA vs μg ConA | Regulation 1 × g vs μg | Fold Change 1 × g ConA vs NT | Regulation 1 × g vs NT |
|---|---|---|---|---|---|
| hsa-mir-6860 | 0.02 | 1.81 | up | 1.60 | up |
| hsa-mir-1976 | 0.04 | 2.54 | up | 1.79 | up |
| hsa-mir-550b-1 | 0.03 | 2.31 | up | 1.74 | up |
| hsa-mir-550b-2 | 0.03 | 2.31 | up | 1.74 | up |
| hsa-miR-8071 | 0.04 | 3.25 | up | 3.01 | up |
| hsa-miR-4481 | 0.04 | 1.97 | up | 1.90 | up |
| hsa-mir-3689b | 0.03 | 1.80 | up | 1.89 | up |
| hsa-miR-629-3p | 0.03 | -3.16 | down | -5.06 | down |
| hsa-miR-330-3p | 0.03 | -2.64 | down | -3.20 | down |
| hsa-miR-501-3p | 0.04 | -2.82 | down | -3.34 | down |
| *hsa-miR-7-1-3p* | *0.01* | *-6.14* | *down* | *-5.63* | *down* |
| *hsa-miR-128-3p* | *0.01* | *-3.06* | *down* | *-4.85* | *down* |
| *hsa-miR-26b-5p* | *0.05* | *-11.28* | *down* | *-11.55* | *down* |
| *hsa-miR-125b-5p* | 0.01 | *-6.37* | *down* | *-5.96* | *down* |
| hsa-miR-99a-5p | 0.00 | -9.60 | down | -7.20 | down |
| *hsa-miR-363-3p* | *0.01* | *-7.69* | *down* | *-7.03* | *down* |

Example 2

Increasing T Cell Activation in a Subject with Decreased Immune Response

In this example, a sample including T cells (such as a blood sample) is removed from a subject, for example a subject with decreased immune response, such as a subject infected with HIV. In some examples, T cells are isolated from the sample. The T cells (either isolated T cells or T cells present in the sample from the subject) are incubated with agents to activate the T cells (such as an antigen presenting cell with an MHC molecule bound to an antigen, anti-CD3 antibodies (if the subject is human), or anti-CD28 and ConA (if the subject is a mouse) for a sufficient amount of time to activate the T cells in the sample. The activated T cells are further incubated in vitro with an effective amount of a miRNA (such as mir-326, miR-6860, mir-6860, mir-1976, mir-550b-1, mir-550b-2, miR-8071, miR-4481, or mir-3689, or a mimic thereof) or a miRNA inhibitor (such as an inhibitor of miR-25-3p, miR-629-3p, miR-330-3p, miR-501-3p, miR-7-1-3p, miR-128-3p, miR-26b-5p, miR-125b-5p, miR-99a-5p, or miR-363-3p 2, or a mimic thereof), such that the activation of the T cells is increased (for example as compared to the activated T cells that have not been incubated with the miRNA or miRNA inhibitor). The resulting T cells with increased activation are re-introduced to the subject with the decreased immune response, in an amount sufficient to treat the symptoms of the decreased immune response.

Example 3

Decreasing T Cell Activation in a Subject with Inflammatory or Autoimmune Disorder In this example, a sample including T cells (such as a blood sample) is removed from a subject, for example a subject with an inflammatory or autoimmune disorder, such as a subject with rheumatoid arthritis. In some examples, the sample includes activated T cells (for example, a subject undergoing a cytokine storm). In some examples, activated T cells are isolated from the sample. The activated T cells (either isolated T cells or T cells present in the sample from the subject) are incubated in vitro with an effective amount of a miRNA inhibitor (such as an inhibitor of mir-326, miR-6860, mir-6860, mir-1976, mir-550b-1, mir-550b-2, miR-8071, miR-4481, or mir-3689, or a mimic thereof) or a miRNA (such as miR-25-3p, miR-629-3p, miR-330-3p, miR-501-3p, miR-7-1-3p, miR-128-3p, miR-26b-5p, miR-125b-5p, miR-99a-5p, or miR-363-3p, or a mimic thereof), such that the activation of the T cells is decreased (for example as compared to the activated T cells that have not been incubated with the miRNA or miRNA inhibitor). The resulting T cells with decreased activation are re-introduced to the subject with the inflammatory or autoimmune disorder, in an amount sufficient to treat the symptoms of the inflammatory or autoimmune disorder.

REFERENCES

1. Hughes-Fulford, M., Chang, T. T., Martinez, E. M., and Li, C. F. (2015) Spaceflight alters expression of microRNA during T-cell activation. *Faseb j* 29, 4893-4900
2. Johnson, R. F., Mitchell, C. M., Giles, W. B., Bisits, A., and Zakar, T. (2006) Mechanisms regulating prostaglandin H2 synthase-2 mRNA level in the amnion and chorion during pregnancy. *The Journal of endocrinology* 188, 603-610
3. Wang, X., Spandidos, A., Wang, H., and Seed, B. (2012) PrimerBank: a PCR primer database for quantitative gene expression analysis, 2012 update. *Nucleic acids research* 40, D1144-1149
4. Agarwal, V., Bell, G. W., Nam, J.-W., and Bartel, D. P. (2015) Predicting effective microRNA target sites in mammalian mRNAs. *eLife* 4, e05005

5. Vlachos, I. S., Paraskevopoulou, M. D., Karagkouni, D., Georgakilas, G., Vergoulis, T., Kanellos, I., Anastasopoulos, I. L., Maniou, S., Karathanou, K., Kalfakakou, D., Fevgas, A., Dalamagas, T., and Hatzigeorgiou, A. G. (2015) DIANA-TarBase v7.0: indexing more than half a million experimentally supported miRNA:mRNA interactions. *Nucleic acids research* 43, D153-159

In view of the many possible embodiments to which the principles of the disclosure may be applied, it should be recognized that the illustrated embodiments are only examples and should not be taken as limiting the scope of the invention. Rather, the scope of the invention is defined by the following claims. We therefore claim as our invention all that comes within the scope and spirit of these claims.

I claim:

1. A method for altering T cell activation in a subject, comprising:
   (a) selecting a subject with activated T cells; and
      administering to the subject a therapeutically effective amount of:
      (i) an inhibitor of miRNA or a-mimic of the inhibitor of miRNA, wherein the inhibitor of miRNA comprises a nucleic acid at least 90% complementary to an miRNA, wherein the miRNA comprises at least one of miR-7-1-3p, miR-128-3p, miR-26b-5p, miR-125b-5p, miR-363-3p, miR-25-3p, miR-629-3p, miR-330-3p, miR-501-3p, and/or miR-99a-5p; or
      (ii) an miRNA, wherein the miRNA comprises at least one of mir-326, mir-6860, mir-1976, mir-550b-1, mir-550b-2, miR-8071, miR-4481, and/or mir-3689b, or a mimic thereof,
      thereby increasing T cell activation as compared to a control; or
   (b) selecting a subject with activated T cells; and
      administering to the subject a therapeutically effective amount of:
      (i) an miRNA, wherein the miRNA comprises at least one of miR-7-1-3p, miR-128-3p, miR-26b-5p, miR-125b-5p, miR-363-3p, miR-25-3p, miR-629-3p, miR-330-3p, miR-501-3p, and/or miR-99a-5p, or a mimic thereof; or
      (ii) an inhibitor of miRNA or a mimic of the inhibitor of miRNA, wherein the inhibitor of miRNA comprises a nucleic acid at least 90% complementary to an miRNA, wherein the miRNA comprises at least one of mir-326, mir-6860, mir-1976, mir-550b-1, mir-550b-2, miR-8071, miR-4481, and/or mir-3689b, thereby decreasing T cell activation as compared to a control.

2. A method for altering T cell activation in a subject comprising:
(a) activating T cells; and
contacting the activated T cells with an effective amount of:
(i) an inhibitor of miRNA or a-mimic of the inhibitor of miRNA, wherein the inhibitor of miRNA comprises a nucleic acid at least 90% complementary to an miRNA, wherein the miRNA comprises at least one of miR-7-1-3p, miR-128-3p, miR-26b-5p, miR-125b-5p, miR-363-3p, miR-25-3p, miR-629-3p, miR-330-3p, miR-501-3p, and/or miR-99a-5p; or
(ii) an miRNA, wherein the miRNA comprises at least one of mir-326, mir-6860, miR-6860, mir-1976, mir-550b-1, mir-550b-2, miR-8071, miR-4481, and/or mir-3689b, or a mimic thereof,
thereby increasing T cell activation as compared to a control; or
(b) contacting activated T cells with an effective amount of:
(i) an miRNA, wherein the miRNA comprises at least one of miR-7-1-3p, miR-128-3p, miR-26b-5p, miR-125b-5p, miR-363-3p, miR-25-3p, miR-629-3p, miR-330-3p, miR-501-3p, and/or miR-99a-5p, or a mimic thereof; or
(ii) an inhibitor of miRNA or a mimic of the inhibitor of miRNA, wherein the inhibitor of miRNA comprises a nucleic acid at least 90% complementary to an miRNA, wherein the miRNA comprises at least one of mir-326, mir-6860, miR-6860, mir-1976, mir-550b-1, mir-550b-2, miR-8071, miR-4481, and/or mir-3689b, thereby decreasing the T cell activation as compared to a control.

3. The method of claim 1, wherein the T cell comprises a CD4+ T cell, a CD8+ T cell, or a combination thereof.

4. The method of claim 1, wherein:
(a) the inhibitor of miRNA or mimic of the inhibitor of miRNA inhibits at least one of miR-7-1-3p, miR-128-3p, miR-26b-5p, miR-125b-5p, and/or miR-363-3p; or
(b) the miRNA comprises a at least one of miR-7-1-3p, miR-128-3p, miR-26b-5p, miR-125b-5p, and/or miR-363-3p or a mimic thereof.

5. The method of claim 1, wherein the miRNA comprises a pri-miRNA, a pre-miRNA, or a mature miRNA.

6. The method of claim 1, wherein the miRNA is a human miRNA.

7. The method of claim 1, wherein the subject is infected with human immunodeficiency virus, the subject has been or will be exposed to microgravity, or the subject has an inflammatory or autoimmune disorder.

8. The method of claim 7, wherein the inflammatory disorder comprises rheumatoid arthritis, chronic obstructive pulmonary lung disease, inflammatory bowel disease, or systemic lupus erythematosus or wherein the autoimmune disorder comprises multiple sclerosis, ankylosing spondylitis, celiac disease, Crohn's disease, Graves' disease, Hashimoto thyroiditis, or autoimmune uveitis.

9. The method of claim 1, wherein the subject is human.

* * * * *

```
                               SEQUENCE LISTING

<160> NUMBER OF SEQ ID NOS: 27

<210> SEQ ID NO 1
<211> LENGTH: 22
<212> TYPE: RNA
<213> ORGANISM: Homo sapiens

<400> SEQUENCE: 1
cauugcacuu gucucggucu ga                                                 22

<210> SEQ ID NO 2
<211> LENGTH: 95
<212> TYPE: RNA
<213> ORGANISM: Homo sapiens

<400> SEQUENCE: 2
cucaucuguc uguugggcug gaggcagggc cuuugugaag gcggguggug cucagaucgc        60
cucugggccc uuccuccagc cccgaggcgg auuca                                   95

<210> SEQ ID NO 3
<211> LENGTH: 95
<212> TYPE: RNA
<213> ORGANISM: Mus musculus

<400> SEQUENCE: 3
cucaucuguc uguugggcug ggggcagggc cuuugugaag gcgggguuaug cucagaucgc       60 cucugggccc uuccuccagu cccgaggcag auuua                                   95

<210> SEQ ID NO 4
<211> LENGTH: 66
<212> TYPE: RNA
<213> ORGANISM: Homo sapiens

<400> SEQUENCE: 4
guuaagcauu ggggaguuug gagucggugg guggagccaa acugggcagg gcugugguga       60
gugagu                                                                   66

<210> SEQ ID NO 5
<211> LENGTH: 22
<212> TYPE: RNA
<213> ORGANISM: Homo sapiens

<400> SEQUENCE: 5
acugggcagg gcuguggu ga gu                                                22

<210> SEQ ID NO 6
<211> LENGTH: 52
<212> TYPE: RNA
<213> ORGANISM: Homo sapiens

<400> SEQUENCE: 6
gcagcaagga aggcagggu ccuaaggugu guccuccugc ccuccuugcu gu                 52
```

```
<210> SEQ ID NO 7
<211> LENGTH: 20
<212> TYPE: RNA
<213> ORGANISM: Homo sapiens

<400> SEQUENCE: 7
ccuccugccc uccuugcugu                                                    20

<210> SEQ ID NO 8
<211> LENGTH: 97
<212> TYPE: RNA
<213> ORGANISM: Homo sapiens

<400> SEQUENCE: 8
agagacuugu uggagaugug ccugagggag uaagacacua ucuuacaaca acagggcucu        60
uacucccuca ggcacugcac cagccagcaa agcauca                                 97

<210> SEQ ID NO 9
<211> LENGTH: 97
<212> TYPE: RNA
<213> ORGANISM: Homo sapiens

<400> SEQUENCE: 9
agagacucgc uggagaugug ccugagggag uaagacacua ucugacaaca acagggcucu        60
uacucccuca ggcacugcac cagccagcaa agcauca                                 97

<210> SEQ ID NO 10
<211> LENGTH: 20
<212> TYPE: RNA
<213> ORGANISM: Homo sapiens

<400> SEQUENCE: 10
cgguggacug gagugggugg                                                    20

<210> SEQ ID NO 11
<211> LENGTH: 65
<212> TYPE: RNA
<213> ORGANISM: Homo sapiens

<400> SEQUENCE: 11
cggccacaug gcccaggcuc uucuccgagu gaucucggug gacuggagug gguaggu          60 ggcag                                                                    65

<210> SEQ ID NO 12
<211> LENGTH: 17
<212> TYPE: RNA
<213> ORGANISM: Homo sapiens

<400> SEQUENCE: 12
ggagugggcu ggugguu                                                       17

<210> SEQ ID NO 13
<211> LENGTH: 60
<212> TYPE: RNA
<213> ORGANISM: Homo sapiens

<400> SEQUENCE: 13
ggagugggcu ggugguuuuu uaagaggaag ggagaccuaa gcuagcacau gagcacgcuc        60

<210> SEQ ID NO 14
<211> LENGTH: 148
<212> TYPE: RNA
```

<213> ORGANISM: Homo sapiens

<400> SEQUENCE: 14
gauccugugc ucccuggggg gucugauccu gugcuuccug ggaggguguga uaucauggu      60 ccugggaggu gugaucccgu gcuuccuggg aggugugaua uuguggu ucc ugggaggugu    120 gaucccgugc ucccugggag gugugauc                                       148

<210> SEQ ID NO 15
<211> LENGTH: 22
<212> TYPE: RNA
<213> ORGANISM: Homo sapiens

<400> SEQUENCE: 15
ugugauauca ugguuccugg ga                                              22

<210> SEQ ID NO 16
<211> LENGTH: 22
<212> TYPE: RNA
<213> ORGANISM: Homo sapiens

<400> SEQUENCE: 16
cugggaggug ugauauugug gu                                              22

<210> SEQ ID NO 17
<211> LENGTH: 22
<212> TYPE: RNA
<213> ORGANISM: Homo sapiens

<400> SEQUENCE: 17
guucucccaa cguaagccca gc                                              22

<210> SEQ ID NO 18
<211> LENGTH: 23
<212> TYPE: RNA
<213> ORGANISM: Homo sapiens

<400> SEQUENCE: 18
gcaaagcaca cggccugcag aga                                             23

<210> SEQ ID NO 19
<211> LENGTH: 23
<212> TYPE: RNA
<213> ORGANISM: Mus musculus

<400> SEQUENCE: 19
gcaaagcaca gggccugcag aga                                             23

<210> SEQ ID NO 20
<211> LENGTH: 22
<212> TYPE: RNA
<213> ORGANISM: Homo sapiens

<400> SEQUENCE: 20
aaugcacccg ggcaaggauu cu                                              22

<210> SEQ ID NO 21
<211> LENGTH: 22
<212> TYPE: RNA
<213> ORGANISM: Mus musculus

<400> SEQUENCE: 21
aaugcacccg ggcaaggauu ug                                              22

```
<210> SEQ ID NO 22
<211> LENGTH: 22
<212> TYPE: RNA
<213> ORGANISM: Homo sapiens

<400> SEQUENCE: 22
caacaaauca cagucugcca ua                                              22

<210> SEQ ID NO 23
<211> LENGTH: 21
<212> TYPE: RNA
<213> ORGANISM: Homo sapiens

<400> SEQUENCE: 23
ucacagugaa ccgguucucuu u                                              21

<210> SEQ ID NO 24
<211> LENGTH: 21
<212> TYPE: RNA
<213> ORGANISM: Homo sapiens

<400> SEQUENCE: 24
uucaaguaau ucaggauagg u                                               21

<210> SEQ ID NO 25
<211> LENGTH: 22
<212> TYPE: RNA
<213> ORGANISM: Homo sapiens

<400> SEQUENCE: 25
ucccugagac ccuaacuugu ga                                              22

<210> SEQ ID NO 26
<211> LENGTH: 22
<212> TYPE: RNA
<213> ORGANISM: Homo sapiens

<400> SEQUENCE: 26
aacccguaga uccgaucuug ug                                              22

<210> SEQ ID NO 27
<211> LENGTH: 22
<212> TYPE: RNA
<213> ORGANISM: Homo sapiens

<400> SEQUENCE: 27
aauugcacgg uauccaucug ua                                              22
```